United States Patent
Redei

(10) Patent No.: US 11,089,959 B2
(45) Date of Patent: Aug. 17, 2021

(54) ELECTRONIC DELIVERY OF INFORMATION IN PERSONALIZED MEDICINE

(71) Applicant: i2Dx, Inc., San Francisco, CA (US)

(72) Inventor: Janos Redei, San Francisco, CA (US)

(73) Assignee: i2Dx, Inc., San Francisco, CA (US)

(*) Notice: Subject to any disclaimer, the term of this patent is extended or adjusted under 35 U.S.C. 154(b) by 649 days.

(21) Appl. No.: 15/919,666

(22) Filed: Mar. 13, 2018

(65) Prior Publication Data

US 2018/0199815 A1    Jul. 19, 2018

Related U.S. Application Data

(63) Continuation-in-part of application No. 15/714,984, filed on Sep. 25, 2017, now Pat. No. 10,660,522,
(Continued)

(51) Int. Cl.
*A61B 5/00* (2006.01)
*G16H 80/00* (2018.01)
(Continued)

(52) U.S. Cl.
CPC .......... *A61B 5/0022* (2013.01); *G16H 10/60* (2018.01); *G16H 15/00* (2018.01); *G16H 40/67* (2018.01); *G16H 50/20* (2018.01); *G16H 80/00* (2018.01)

(58) Field of Classification Search
None
See application file for complete search history.

(56) References Cited

U.S. PATENT DOCUMENTS

| | | |
|---|---|---|
| 8,093,011 B2 | 1/2012 | Haley et al. |
| 8,108,228 B2 | 1/2012 | Maresh et al. |

(Continued)

FOREIGN PATENT DOCUMENTS

| | | |
|---|---|---|
| CN | 101622622 A | 1/2010 |
| JP | 2003-173376 A | 6/2003 |

(Continued)

OTHER PUBLICATIONS

Giri et al, Genes associated with Alzheimer's disease: an overview and current status, Dove Pres Journal: Clinical Interventions in Aging, May 17, 2016, https://www.ncbi.nlm.nih.gov/pmc/articles/PMC4876682/pdf/cia-11-665.pdf (Year: 2016).*

(Continued)

*Primary Examiner* — Devin C Hein
(74) *Attorney, Agent, or Firm* — Maschoff Brennan

(57) ABSTRACT

According to an aspect of an embodiment, a computer-implemented method of delivering information-enabled personalized health care with respect to early Alzheimer's disease in a clinical, non-research setting, comprising a social network, may include capturing one or more data streams where each of the data streams relates to health care of a patient, wherein the one of the data streams is captured from testing for certain genetic variations including single-nucleotide polymorphisms (SNPs). The method may further include integrating the data streams to generate integrated diagnostic data and analyzing the integrated diagnostic data to generate analyzed diagnostic data. The method may further include curating the analyzed diagnostic data and generating an integrated report for presentation to a physician of the patient based on the curated analyzed diagnostic data.

21 Claims, 16 Drawing Sheets

Related U.S. Application Data which is a continuation of application No. 13/842,004, filed on Mar. 15, 2013, now Pat. No. 9,782,075.

(51) Int. Cl.
| | |
|---|---|
| *G16H 10/60* | (2018.01) |
| *G16H 50/20* | (2018.01) |
| *G16H 15/00* | (2018.01) |
| *G16H 40/67* | (2018.01) |

(56) References Cited

U.S. PATENT DOCUMENTS

| | | | |
|---|---|---|---|
| 8,140,144 | B2 | 3/2012 | Date et al. |
| 8,306,831 | B2 | 11/2012 | Eisenberger et al. |
| 9,663,569 | B2 | 5/2017 | Kami et al. |
| 2004/0015372 | A1 | 1/2004 | Bergman et al. |
| 2006/0036471 | A1 | 2/2006 | Sanjay-Gopal et al. |
| 2006/0099624 | A1 | 5/2006 | Wang et al. |
| 2008/0077431 | A1 | 3/2008 | Calder et al. |
| 2008/0077446 | A1 | 3/2008 | Korpman et al. |
| 2008/0176239 | A1 | 7/2008 | Chissoe et al. |
| 2010/0299155 | A1 | 11/2010 | Findlay et al. |
| 2011/0077973 | A1 | 3/2011 | Breitenstein et al. |
| 2011/0286932 | A1 | 11/2011 | Koronyo et al. |
| 2012/0101843 | A1 | 4/2012 | Mathur et al. |
| 2012/0231959 | A1 | 9/2012 | Elton et al. |
| 2013/0191161 | A1 | 7/2013 | Churchwell et al. |
| 2015/0046176 | A1 | 2/2015 | Xu et al. |
| 2015/0073022 | A1 | 3/2015 | Roses |
| 2015/0141491 | A1 | 5/2015 | Nagy |
| 2016/0355587 | A1 | 12/2016 | West et al. |
| 2018/0020918 | A1 | 1/2018 | Redei |

FOREIGN PATENT DOCUMENTS

| | | | |
|---|---|---|---|
| JP | 2008-276724 A | 11/2008 | |
| JP | 2010-187959 A | 9/2010 | |
| JP | 2011-164956 A | 8/2011 | |
| WO | 2012/148817 A2 | 11/2012 | |
| WO | WO-2012170704 A2 * | 12/2012 | ............. G16C 20/30 |

OTHER PUBLICATIONS

CA Office Action dated Jul. 18, 2018 received in Application No. 2,907,207.
CN Office Action dated Jan. 18, 2019 as reeived in Application No. 201480026650.1.
AU Patent Examination Report No. 3 dated Nov. 26, 2018 as received in Application No. 2017204178.
CN Decision on Rejection dated Oct. 16, 2019 as received in Application No. 201480026650.1.
Extended European Search Report dated Jun. 21, 2018 as received in Application No. 14764506.
JP Notice of Allowance dated Oct. 24, 2017 as received in Application No. 2016-502903 [English Translation].
CA Office Action dated Apr. 28, 2017 as received in Application No. 2907207.
KR Office Action dated Dec. 16, 2016 as received in Application No. 10-2015-7029307 (English Translation).
JP Office Action dated Nov. 22, 2016 as received in Application No. 2016-502903 (English Translation).
International Search Report dated Aug. 28, 2014 as received in Application No. PCT/US2014/028800.
Written Opinion of the International Searching Authority dated Aug. 28, 2014 as received in Application No. PCT/US2014/028800.
Chen et al., Classification of Alzheimer Disease, Mild Cognitive Impairment, and Normal Cognitive Status with Large-Scale Network Analysis Based on Resting-State Functional MR Imaging, Apr. 2011, Radiology, vol. 259, No. 1, pp. 213-221.
Goodin et al., Disease modifying therapies in multiple sclerosis, Neurology, vol. 59(3), pp. 472-473, Aug. 13, 2002.

CA Office Action dated Jul. 9, 2019 as received in Application No. 2907207.
AU Patent Examination Report No. 2 dated Jun. 28, 2018 as received in Application No. 2017204178.
Thelen, Karten et al., "Translation of the cell adhesion molecule ALCAM in axonal growth cones—regulation and functional importance", Journal of Cell Science 125 (4), 2012, pp. 1003-1014, Published by the Company of Biologists Ltd, doi: 10.1242/jcs.096149.
Li, Yan et al., "CD6 as a potential target for treating multiple sclerosis", PNAS Early Edition, Accepted Jan. 25, 2017, pp. 1-6, www.pnas.org/cgi/doi/10.1073/pnas.1615253114.
Von Bauer, Rudiger, et al., "CD166/ALCAM Mediates Proinflammatory Effects of S100B in Delayed Type Hypersensitivity", The Journal of Immunology, 2013, 191: 369-377, www.jimmunol.org/cgi/doi/10.4049/immunol.1201864.
Lecuyer, Marc-Andre et al., "Dual role of ALCAM in neuroinflammation and blood-brain barrier homeostatsis", PNAS, Jan. 9, 2017, pp. ES24-ES33, www.pnas.org/cgi/doi/10.1073/pnas.1614336114.
Hansen, Amanda G. et al., "ALCAM: Basis Sequence: Mouse", AFCS Nat Mol Pages Author manuscript, available in PMC May 15, 2015, published in final edited form as: AFCS Nat Mol Pages. 2011, pp. 1-12.
Song, Bing et al., "Inhibition of Polo-like kinase 1 reduces beta-amyloid-induced neuronal cell death in Alzheimer's disease", Aging, Sep. 2011, vol. 3, No. 9, pp. 846-851.
Fischer, Peter M. (2017) Approved and experimental small-molecule oncology kinase inhibitor drugs: a mid-2016 overview. Medicinal Research Reviews, 37 (2). pp. 314-367. ISSN 1098-1128.
Alalawi, Fakhriya et al., "m-TOR Inhibitors in the Current Practice", Journal of Clinical & Experimental Nephrology, 2017, vol. 2, No. 1:26, pp. 1-16, DOI: 10.21767/2472-5056.100026.
Kumar, Shiv et al., "Regulatory functional territory of PLK-1 and their substrates beyond mitosis", Oncotarget, 2017, vol. 8, (No. 23), pp. 37942-37962.
Miron, Justin et al., "CDK5RAP2 gene and tau pathophysiology in late-onset sporadic Alzheimer's disease", Alzheimer's & Dementia, (2018) 1-10, Published by Elsevier Inc. on behalf of the Alzheimer's Association., https://doi.org/10.1016/j.jalz.2017.12.004.
Chen, Hsin-Yi et al., "Human microcephaly protein RTTN interacts with STIL and is required to build full-length centrioles", Nature Communications, 8:247, DOI: 10.1038/s41467-017-00305-0.
Xu, Haiwei et al., "The function of BMP4 during neurogenesis in the adult hippocampus in Alzheimer's disease", Ageing Research Reviews 12 (2013) 157-164, http://dx.doi.org/10.1016/j.arr.2012.05.002.
Yousef, Hanadie et al., "Age-Associated Increase in BMP Signaling Inhibits Hippocampal Neurogenesis", Stem Cells 2015;33:1577-1588, http://dx.doi.org/10.1002/stem.1943.
Eid, Ayman et al., "Genome editing: the road of CRISPR/Cas9 from bench to clinic", Experimental & Molecular Medicine (2016) 48, e265; doi:10.1038/emm.2016.111.
Liao, Hsin-Kai et al., "In Vivo Target Gene Activation via CRISPR/Cas9-Mediated Trans-epigenetic Modulation", Cell, 171, 1-13, Dec. 14, 2017, Elsevier Inc., https://doi.org/10.1016/j.cell.2017.10.025.
Obregon, Pazos et al., "Putative synaptic genes defined from a *Drosophila* whole body developmental transcriptome by a machine learning approach", BMC Genomics (2015) 16:694 DOI 10.1186/s12864-015-1888-3.
Karaca, Ilker et al., "Functional Characterization of a Rare Genetic Variant in Phospholipase Cg2 Which Is Associated With a Beneficial Effect on the Progression of Alzheimer's Disease", (P3-164) Poster Presentations: Tuesday, Jul. 18, 2017, p. 997.
Yan, Yan et al., "The Vacuolar Proton Pump, V-ATPase, Is Required for Notch Signaling and Endosomal Trafficking in *Drosophila*", Developmental Cell 17, 387-402, Sep. 15, 2009, DOI 10.1016/j.devcel.2009.07.001.
Ravikumar, Brinda et al., "Dynein mutations impair autophagic clearance of aggregate-prone proteins", Nature Genetics, vol. 37, No. 7, Jul. 2005, Published online Jun. 26, 2005; doi:10.1038/ng1591.
Cai, Qian et al., "Mitochondrial Aspects of Synaptic Dysfunction in Alzheimer's Disease", J Alzheimers Dis., Author manuscript; avail-

(56) References Cited

OTHER PUBLICATIONS able in PMC Apr. 24, 2017. Published in final edited form: J Alzheimers Dis. 2017 ; 57(4): 1087-1103. doi:10.3233/JAD-160726.

Desikan, Rahul S. et al., "Genetic assessment of age-associated Alzheimer disease risk: Development and validation of a polygenic hazard score", PLOS Medicine, Mar. 21, 2017, pp. 1-17, DOI:10.1371/journal.pmed.1002258.

Gant, John C. et al., "FK506-Binding Protein 12.6/1b, a Negative Regulator of [Ca2+], Rescues Memory and Restores Genomic Regulation in the Hippocampus of Aging Rats", The Journal of Neuroscience, Jan. 24, 2018 • 38(4):1030-1041.

Kia, Sima Kheradmand et al., "RTTN Mutations Link Primary Cilia Function to Organization of the Human Cerebral Cortex", The American Journal of Human Genetics 91, 533-540, Sep. 7, 2012, http://dx.doi.org/10.1016/j.ajhg.2012.07.008.

McQuate, Andrea et al., "A Wnt/Calcium Signaling Cascade Regulates Neuronal Excitability and Trafficking of NMDARs", 2017, Cell Reports 21, 60-69 Oct. 3, 2017 (c) 2017 The Author(s). https://doi.org/10.1016/j.celrep.2017.09.023.

AU Patent Examination Report No. 1 dated Apr. 10, 2018 as received in Application No. 2017204178.

EP Office Action dated Mar. 5, 2020 as received in Application No. 14764506.3.

Ishiguro et al., "Activated Leukocyte Cell-Adhesion Molecule (ALCAM) Promotes Malignant Phenotypes of Malignant Mesothelioma"; Journal of Thoracic Oncology vol. 7, Issue 5, pp. 890-899, May 212.

Mostafavi, et al., "Identifying Genetic Variants That Affect Viability in Large Cohorts"; PLOS Biol, Sep. 2017.

Park et al., "A Genome-Wide Crispr Screen Identifies a Restricted Set of HIV Host Dependency Factors"; Nat. Genet. Feb. 2017, 49(2), pp. 193-203.

International Search Report and Written Opinion issued for corresponding PCT Application No. PCT/US2019/021945, dated Jul. 2, 2019.

* cited by examiner

ELECTRONIC DELIVERY OF INFORMATION IN PERSONALIZED MEDICINE

CROSS-REFERENCE TO OTHER APPLICATIONS

This patent application is a continuation-in-part of U.S. application Ser. No. 15/714,984 filed Sep. 25, 2017, which is a continuation of U.S. application Ser. No. 13/842,004, filed on Mar. 15, 2013 now U.S. Pat. No. 9,782,075, which is incorporated herein by reference.

FIELD

The embodiments discussed herein are related to electronic delivery of information in personalized medicine.

BACKGROUND

Medicine is becoming increasingly personalized, meaning that treatments are tailored to a patient's individual health data, including genotypic and phenotypic data. Genotypic data may include selected genetic markers, single nucleotide polymorphisms (SNPs), or the entire gene sequence. Phenotypic data may include physical exam data from a patient, clinical scores and rating scales, laboratory results such as from in-vitro tests, and in-vivo imaging data such as magnetic resonance imaging (MRI) scans. Cost of sequencing is falling rapidly due to novel technology such as next-generation sequencing (NGS) and it is foreseeable that such data will become as ubiquitous and low-cost as an MRI scan. Wearable sensors embedded in consumer electronic devices such as accelerometers and mobile electrocardiogram (ECG) are emerging and provide means of continuously measuring phenotypic data in real time, via the Internet, giving rise to "digital health."

Diagnostics is the first step in defining the precise nature of a patient's disease state, typically involving physical measurements that are transformed into digital information such as a MRI scan into a file in the DICOM image format. Laboratory data can be transformed into a portable document format (PDF) file or delivered in a structured Health Layer 7 (HL7) format. Patient's disease states can subsequently be "stratified" based on common characteristics, and a tailored treatment regimen then be chosen that achieves optimized outcomes for the patient.

Alzheimer's disease (AD) diagnosis is complex, particularly in the early stages of disease (prodromal or pre-symptomatic disease). Diagnosis may include clinical scores (such as cognitive testing) and sophisticated biomarkers such as quantitative MM data. Patients with cognitive problems are typically first seen by a busy non-specialist primary care physician (PCP) who may eventually refer the patient to a specialist memory clinic; however, the early diagnosis of Alzheimer's disease is often delayed by several years after the first cognitive symptoms. Exams are repeated because they have quality issues and lack standardization, or simply because the specialist did not have access to the previous exams, often because data could not be shared easily. Sometimes a costly PET scan is ordered by a primary care physician very early in the process, without staging the diagnostic process first from low-cost screening to confirmatory diagnostics to increase diagnostic certainty in a step-wise manner.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method of delivering information-enabled personalized healthcare in a clinical, non-research setting may include capturing one or more data streams where each of the data streams relates to health care of a patient. The method may further include integrating the data streams to generate integrated diagnostic data and analyzing the integrated diagnostic data to generate analyzed diagnostic data. The method may further include curating the analyzed diagnostic data and generating an integrated report for presentation to a physician of the patient based on the curated analyzed diagnostic data.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Some embodiments herein describe methods and systems for a digital health platform for personalized medicine, particularly in the field of Alzheimer's disease diagnostics. The disclosure describes the integration of various data streams, captured from physical measurements of a patient's disease state, and the electronic routing of such information between primary care physicians and specialists, and a data analytics center to facilitate diagnostics and delivery of personalized treatments in Alzheimer's disease and other diseases. The system incorporates a scalable cloud-based social network architecture that manages the Health Insurance Portability and Accountability Act (HIPAA) compliant exchange of personal health information, including encrypted file transfer and messaging, between the participants of the social network. The exchange of diagnostic information is permission-based and allows referrals to specialists to improve the diagnostic certainty, and is augmented by a data analytics center.

The cloud-based social network architecture allows health care providers to collaborate on a patient case efficiently and share the data in a regulatory compliant manner. Furthermore, the data analytics center of the cloud-based social network architecture allows for optimizations in the diagnostic workflow between health care providers as well as reduces unnecessary exams, improves quality of the data and diagnostic utility, and helps to enable non-specialist physicians to utilize best practices.

Embodiments of the present invention will be explained with reference to the accompanying drawings.

Figure 1:
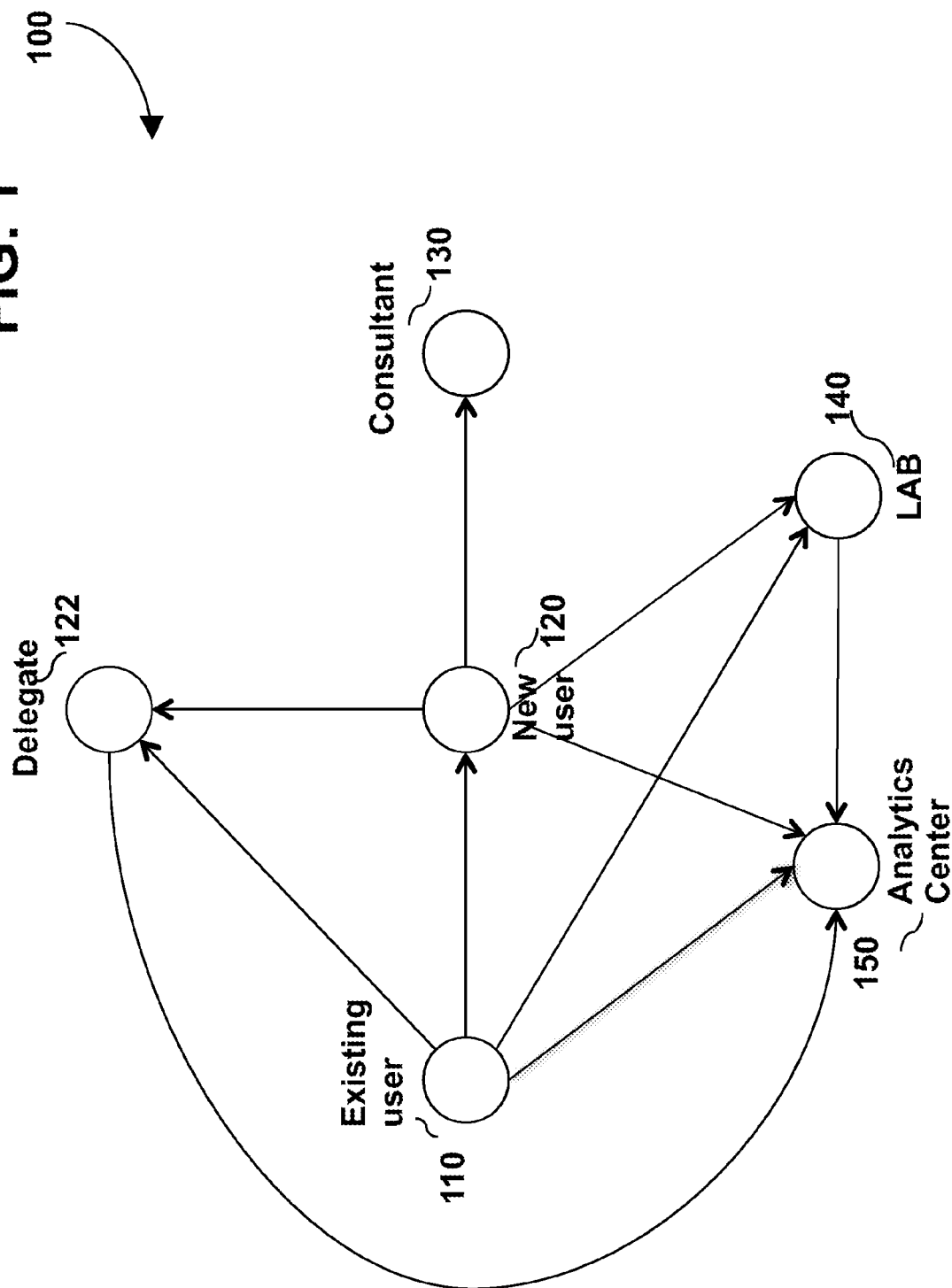
FIG. 1 is a diagram illustrating an example social network for personalized medicine.

FIG. 1 is a diagram illustrating an example social network 100 for personalized medicine, arranged in accordance with at least some embodiments described herein. The social network illustrates various participants, including an existing user 110, a new user 120, a delegate 122, a consultant 130, a lab 140, and a data analytics center 150. Various operations may be performed with respect to the social network 100 and the participants within the social network 100. For example, a participant may be added to the social network 100, participants in the social network 100 may collaborate with respect to medical care of a patient, and data with respect to medical care of a patient may be integrated and analyzed.

To add a participant to the social network, the participant may first be identified. For example, the existing user 110, which may be a primary care physician, may identify the new user 120, which may be a specialty neurologist, to be added to the social network 100. The existing user 110 may have the option to search an external provider database such as the National Plan and Provider Enumeration System (NPPES) to obtain initial contact information for the new user 120. The existing user 110 may also verify the correct electronic contact information, for instance, through telephone.

When a participant is being added to the social network 100, the participant may designate a participant in a private portion of the social network 100 or a non-private portion of the social network 100. In some embodiments, the private portion of the social network 100 may be for participants that are associated with a hospital network. In some embodiments, the social network 100 may have multiple private portions. As an example of designation of a participant in a private portion of the social network 100, the existing user 110 may designate the new user 120 to become part of a private portion of the social network 100 when the new user 120 is part of a hospital network with which the existing user 110 is associated. In these and other embodiments, the consultant 130 may be an external participant, such as a nuclear medicine specialist outside of the hospital network, which can perform a positron emission tomography (PET) scan or other diagnostic tests.

The new user 120 may be added to the social network 100 in various ways. For example, in some embodiments, the new user 120 may be added to the social network using an invitation. The existing user 110 may enter basic information into a system used to support the social network 100, such as the system described with respect to FIG. 9, to initiate contact electronically, such as the new user's 120 e-mail and name. After entering the basic information or indicating the basic information for the new user 120, the existing user 110 may send the new user 120 an invitation to join the social network 100 for personalized medicine. In some embodiments, the invitation to the new user 120 may be automatically generated from a template after the existing user 110 indicates the identity of the new user 120.

The invitation may be sent out by e-mail or other messaging system and contain a link to the login page of the social network 100. An initial password for the new user 120 to access the social network 100 may also be created automatically. The initial password, for security purposes, may be sent out by a separate message, or delivered by calling the new user 120 in an office or on a mobile phone of the new user 120. In some embodiments, password authentication may be augmented or replaced by biometric identity verification such as fingerprint, speech, face recognition, and/or another electronic access control system. The another electronic access control system may include, as examples and without limitation, a card-based and a smartphone equipped with electronic identity verification. In some embodiments, the authentication method may be a multifactor authentication such as a two-factor authentication (TFA), which may use the presentation of two or more of three authentication factors, such as a knowledge factor (such as the password), a possession factor (such as a special access card issued by the social network provider), and an inherence factor (such as a biometric factor, e.g., voice or video authentication).

After a user receives an invitation to be part of the social network 100, the new user 120 completes the registration process by changing the initial password to a secure-format password of his/her choice (such as having a certain length and characters), and entering additional information, for instance, professional details, address, and other contact information such as pager, mobile phones, fax number, preferences, etc. into a form.

In some embodiments, the registration process may not require the new user 120 to enter a password or adding any additional information regarding the new user 120. For example, authentication may only consist of TFA, as described above. In these and other embodiments, the TFA may consist of distributing a special access card for the social network 100 or some other access information after verifying the new member's credentials and obtaining a biometric factor. In some embodiments, the biometric factor may be obtained by the existing user 110 from the new user 120, for example at a medical conference. Additional information about the new user 120 may also be obtained through other sources, such as a provider database or credentialing authorities. The additional information may be prepopulated into the form for the new user 120 to ease the registration process for the new user 120 while maintaining security and privacy.

In some embodiments, when the new user 120 is part of the private portion of the social network 100, an administrator associated with the private portion of the social network 100 may add the new user 120 through an administration module that is associated with the social network 100. The administrator may be the existing user 110 and/or the administrator may be another participant in the social network 100 that is not illustrated in FIG. 1. In these and other embodiments, the administrator may limit the participants' permissions within the social network 100 with respect to the ability of the participants to invite new members, receive, and/or refer/send cases within the social network 100.

In some embodiments, when the new user 120 is added to the social network 100, the new user 120 may be associated with the delegate 122, such as a nurse practitioner or physician assistant that acts on behalf of the new user 120. In these and other embodiments, an administrator may add the delegate 122 through the administration module. In some embodiments, the social network 100 may be searchable for participants within the social network 100 for collaboration purposes, such as for inviting participants within the social network 100 to collaborate with respect to medical care of a patient.

The social network 100 may further be configured to allow participants within the social network to communicate regarding a particular treatment using bidirectional secure messaging communication and/or video/voice conferencing within the social network 100. Alternately or additionally, participants within the social network may communicate using a tailored mobile communication application. Existing communication channels such as text (SMS) messaging, pagers, or e-mail may further be utilized as well for nonsecure messaging/alerting. For example, the nonsecure messaging may be used for indicating to a physician that his/her attention is required, or to notify participants of recent activity such as that information has been changed, added, or updated with respect to a patient.

As mentioned previously, participants may collaborate with respect to medical care of a patient. Medical care of a patient as used herein may be referred to herein as a patient case or case. As indicated, participants within the social network 100 may collaborate on a patient case. This collaboration may take place based on a referral process. For example, the existing user 110, which may be a primary care physician (PCP), may refer a patient case to the new user 120, such as a specialist, after the new user 120 has joined the social network 100 or to the lab 140 for further diagnostic evaluation. The existing user 110 may serve as the "patient case owner" during a particular episode of patient care and enter basic patient case data, for example, patient details such as name, gender, date of birth, contact information, and insurance information. The existing user 110 may further enter descriptive information for the case such as priority, type of referral, expected response to referral, and case summary information. The descriptive information such as the summary information may further be imported from another health management system, for example, an electronic medical record (EMR) system. The existing user 110 may further refer a case to multiple members within a private portion of the social network 100 or within the entire social network 100 in order to collaborate on a case. For example, the existing user 110 may refer a case to the consultant 130 during an episode of care (e.g., a phase of treatment) until the episode of care is considered completed by the existing user 110.

The collaboration about a case between the participants within the social network 100 may include sharing information with the participants to determine about the case (e.g., patient test result, lab result, diagnostics, patient history, etc.). In some embodiments, the social network 100 may include a cloud storage for storing information about cases. The participants in the social network 100 associated with the case may be able to access the cloud storage for the case and add information to or retrieve information from the cloud storage. Adding information to the cloud storage or retrieving information from the cloud storage for a particular case may be referred to herein as adding information to the case or retrieving, viewing, or accessing information from the case. Because the case information is part of the social network 100, the participants within the social network 100 associated with the case may access information from the case that other participants have added to the case.

For example, the existing user 110 may add additional case content (along with accompanying metadata/descriptive information) to a case. The additional case content may include the result of a cognitive screening test, genetic test, and/or a blood test for a disease, such as Alzheimer's disease. The test results may be provided in electronic format such as a test report in the PDF document format. The report may be added to the case by file upload or directly from another health management system such as an electronic medical record (EMR) system. Medical images may be added to the case in a similar manner. For example, medical images may be added to the case by the uploading of Digital Imaging and Communications in Medicine (DICOM) files or directly from a picture archiving and communication system (PACS). Information from tests, such as a cognitive screening test on a mobile device, which are performed at the patient's home, may be added to the case. Alternately or additionally, information from tests from a PCP or specialists' offices that have or have not been further augmented by a third party service provider, for instance, a lab service or a data analytics center, may be added to the case. In some embodiments, the information that may be added to the case in the form of test result and/or report may contain normative and/or age-related ranges, plots of the patient's individual value in relation to the normative and/or age-related ranges, and medical images of the patient or representative illustrative other cases. The information that may be added to the case in the form of test result and/or report may further contain context and/or interpretative information such as pointing to a URL or a publication, or including an excerpt or summary of one or many publications.

The collaboration between participants in the social network 100 may be facilitated by a participant requesting review from another participant. For example, the existing user 110, which may be a PCP, may request the new user 120, such as a specialist, to join the social network 100 and to be associated with a case in the social network 100. Alternately or additionally, the existing user 110 may identify that the new user 120 is part of the social network 100 using the social network or some other method, such as a directory website outside the social network 100. In these and other embodiments, the existing user 110 may request that the new user 120 collaborate on a case with the existing user 110. The request may be issued in the manner analogous as that described above or in a different manner. After the new user 120 is set to start collaborating on the case, the existing user 110 may send the case to the new user 120 for further evaluation and/or review. In some embodiments, existing user 110 may indicate to the new user 120 that information has been added to the case for the new user 120 to review. As discussed, the indication of new information may be performed manually, for example, by messaging, or automatically after the new information is added to the case.

For example, the existing user 110 may send a patient case to the new user 120, where the existing user 110 is a PCP and the new user 120 is a consulting neurologist, for further evaluation. The further evaluation may include a comprehensive neurological and/or neuropsychological exam by means of a computerized cognitive battery. Before sending the patient case to the new user 120, the existing user 110 may have added case contents such as screening test results and/or other information such as patient history and medications, and a case summary for the new user 120. The new user 120 may review the case summary information and related messages with secure mobile messaging or by a mobile case dashboard application provided by the social network 100 for viewing information about a case. The dashboard application may allow previewing of available case contents, for example, reports or already-existing images such as magnetic resonance imaging (MRI) or PET scans.

In some embodiments, a dashboard application may be navigated through a natural user interface (NUI) driven by speech, touch, gestures, eye tracking, and other input. The dashboard application may be rendered onto a variety of mounted or projected displays and/or flexible or wearable display devices such as eyeglasses capable of displaying context-aware superimposed information (augmented reality). In some embodiments, the dashboard application may further be a browser-based application with or without NUI input and allow download of case contents such as images for further review on third party viewers or applications such as DICOM image viewer. In these and other embodiments, the browser-based dashboard application may be used within a secure enterprise-computing environment, for example, on a dedicated workstation or access devices within a firewall of a hospital, medical center, doctor office, or some other firewall.

When information is added to a case, such information being an image or laboratory or cognitive test data, the information may have been obtained without stringent quality standards in place and/or may not be in a form that is comparable between cases or within the same case. As a result, the information may not be suitable for further analysis, which may include quantitative image analysis, next-generation sequencing (NGS) genome analytics, or gene expression analysis. To ensure comparable data elements within a case and between cases, information added to a case may be checked for adherence to quality standards by the data analytics center 150. For example, data may be checked for certain source data acquisition parameters and equipment used, prior to further processing, such as automated analysis of an amyloid PET scan, hippocampal volume quantitation, or DTI fiber tractography using MRI imaging. When information does not meet a certain standard, for example, if information does not allow for suitable quantitation, a message may be sent back to the participant that sent the information or to other participants connected to the case.

In some embodiments, the information shared on a case within the social network 100 may not be in a quantitative form. For example, an image produced by an MRI or PET scan may not have quantitative information associated with the image; however, quantitative information may be derived from the image. In these and other embodiments, image data and other information that is not quantitative in nature may have quantitative image analysis performed to aid diagnosis and to share with other participants in the social network. For example, a radiologist may have quantitative analysis performed for longitudinal comparison and/or treatment decision making. Quantitative image analysis may be performed in addition to a qualitative read of scans such as MRI to exclude other disease or aid differential diagnosis, and may be summarized in a qualitative report. Quantitative image analysis may be fully automated or semiautomated with operator interaction, and be performed on site/premises on a workstation or server appliance. The quantitation data or results may then be imported to the case. In some embodiments, quantitative image analysis may be performed on demand at the data analytics center 150 separate from where the information is gathered. In some embodiments, quantitative image analysis may generate a report, such as in PDF format, that contains normative and/or age-related ranges and plots of a patient's individual quantitative imaging values, for example, hippocampal volumes, in relation to the normative and/or age-related ranges. The report may also include selected images of the patient. The quantitative imaging report may be interactive and allow viewing of actual medical images in 2-D, 3-D, or 4-D (3-D, over time) and include advanced visualization features such as plots of quantitative values overlaid with their respective source images, when data points are selected.

It is to be understood that data in known medical reports and even EMRs currently is qualitative and text-based (often free text), allowing a great degree of variability and fuzziness in language. However, it is desirable to have data in quantitative form or utilize a standardized vocabulary (ontology) such as Systematized Nomenclature Of Medicine Clinical Terms (SNOMED). Mandating a particular data type, however, may limit utilizing all existing medical information available in a patient case. To resolve these issues, content curation may be used as an intermediate step for sophisticated capabilities such as integrated reporting, search, semantic integration, and data mining/advanced analytics. Existing quantitative data may be compiled into concise integrated reporting formats presenting one or several biomarkers alongside contextual information such as medical guidelines and/or relevant excerpts from medical literature or links to the original references. In some embodiments, key original references may be included in their entireties in the integrated report. Existing nonstandard information, such as text data, may be annotated using standardized vocabularies for subsequent processing such as search, semantic integration, and data mining purposes. Content curation may utilize fully automated or semiautomated auto-curation software tools and databases at the data analytics center 150, or, after anonymization of data, third-party on-demand services such as Amazon Mechanical Turk.

In some embodiments, the data analytics center 150 may be configured to generate an integrated digital diagnostics report after performing quality control, quantitative image analysis, and curation steps. The integrated digital diagnostics report may combine one or several biomarkers or outcome measures gathered from the lab 140, the new user 120, the existing user 110, the delegate 122, the consultant 130, and/or other participants within the social network 100 collaborating on a case. The data analytics center 150 may then curate the shared information into a consolidated view for assessment by a physician, such as the existing user 110. In some embodiments, the report may be embodied in a mobile application. In some embodiments, the report may further provide longitudinal information on biomarkers or outcome measures in the form of plots or other advanced visualizations described above. In some embodiments, the existing user 110 or some other participant within the social network 100 that is reading the report may consult with an expert physician (proficient in interpreting the integrated data in the report) in a call center by messaging within the social network and as part of a value-added diagnostic service.

In some embodiments, personally-identifiable information, such as names, date of birth, address, and other patient identifying information, may be stripped from information within the social network 100 during an anonymization process. In some embodiments, third party or open source data anonymization software tools may be employed in the data analytics center 150 to provide the anonymization process. An example anonymization process may include removing patient identifying information in DICOM image headers. Anonymization may be fully automated (such as when the data is in a standardized format) or semiautomated. In some embodiments, patient data may be anonymized within the social network 100. The social network 100 may assign the patient data a temporary or permanent unique identification (UID). The social network 100 may allow the physician interacting with the patient associated with the patient data to associate the patient data with a particular case or patient. In some embodiments, the temporary or permanent unique identification (UID) assigned to the patient data may be used in conjunction with diagnostic services such as home-based screening. For example, a patient may obtain a prepaid card with the UID included in a pharmacy. The patient may then visit a PCP that is part of the social network 100. The PCP may request an anonymized integrated screening report from the data analytics center 150, and further consult an expert physician (proficient in interpreting biomarker combinations/patterns) in a call center, by messaging within the social network 100, and as part of a value-added diagnostic service. In these embodiments, the expert physician and the data analytics center 150 may not know the identity of the patient. Rather the expert physician and the data analytics center 150 may only associate the data with the associated UID. Thus, the identity of the patient may remain confidential within the social network 100 even when the case of the patient is worked on by various participants in the social network 100.

In some embodiments, the social network 100 may aggregate data collected in various cases. For example, following quality control, curation, and anonymization steps performed in the data analytics center 150, the data from multiple cases may be aggregated in a centralized or federated database, and advanced analytics run against the database. Non-imaging and/or non-sequencing data may be stored in a SQL or NoSQL database (such as Cassandra), while media-rich contents such as imaging or NGS source data may be stored in file systems for performance reasons. The database may support semantic data integration to interrelate with data from other databases and datasets. The file system storage may be distributed such as in Hadoop Distributed File System (HDFS). Image files may reside in an external image repository optimized for performance and referred to by a URL link or other pointer stored in the database.

After data from one or more cases is aggregated into a database, various advanced "big data" analytics may be run against the aggregated data. The advanced analytics may include the process of examining large amounts of data of a variety of types to uncover hidden patterns, unknown correlations, and other useful information. The advanced analytics may be performed in the data analytics center 150. For example, the advanced analytics may include predictive analytics based on machine learning algorithms and/or data mining or statistical analysis techniques (e.g., using R). The advanced analytics may be distributed (such as in Map Reduce) or parallelized. For example, advanced analytics may predict treatment response, or future onset of disease, in a pre-symptomatic Alzheimer's disease patient based on a biomarker pattern and/or genetic profile combination, or calculate a probability of current disease given a certain combination of factors that are included in the case information within the database. Advanced analytics may further be used to run sophisticated predictive analytics which may be based on a PET scan (for instance, fully automated amyloid PET or tau tracer quantification). Alternately or additionally, the sophisticated predictive analytics may be based on a predictive brain network "connectome" analysis based on diffusion tensor imaging (DTI) MRI or functional MRI. The advanced analytics may be performed on a particular case to assist in determining a diagnosis, treatment, or other aspect related to the particular case within the social network 100.

In some embodiments, the advanced analytics may further include use of semantic searches against the aggregated data repository to discover and rank cases with known treatment outcome similar to a particular case in order to provide a personalized treatment in the particular case. The results of the advanced analytics may be summarized or otherwise presented in a report. In some embodiments, the report may be accessed by a participant in the social network 100 through a personalized health care (PHC) tailored dashboard that may be driven by a natural user interface (NUI), as described above.

In some embodiments, the advanced analytics may further be performed by data scientists. The data scientist may derive new knowledge from the aggregated database that may aid diagnostic certainty and/or provide therapeutic stratification in a particular case.

Modifications, additions, or omissions may be made to the social network 100 without departing from the scope of the present disclosure. For example, the social network 100 may include other participants than those described above. Furthermore, the social network 100 may include various other aspects than those described above. For example, other aspects of the social network may be described with respect to other Figures herein.

Figure 2:
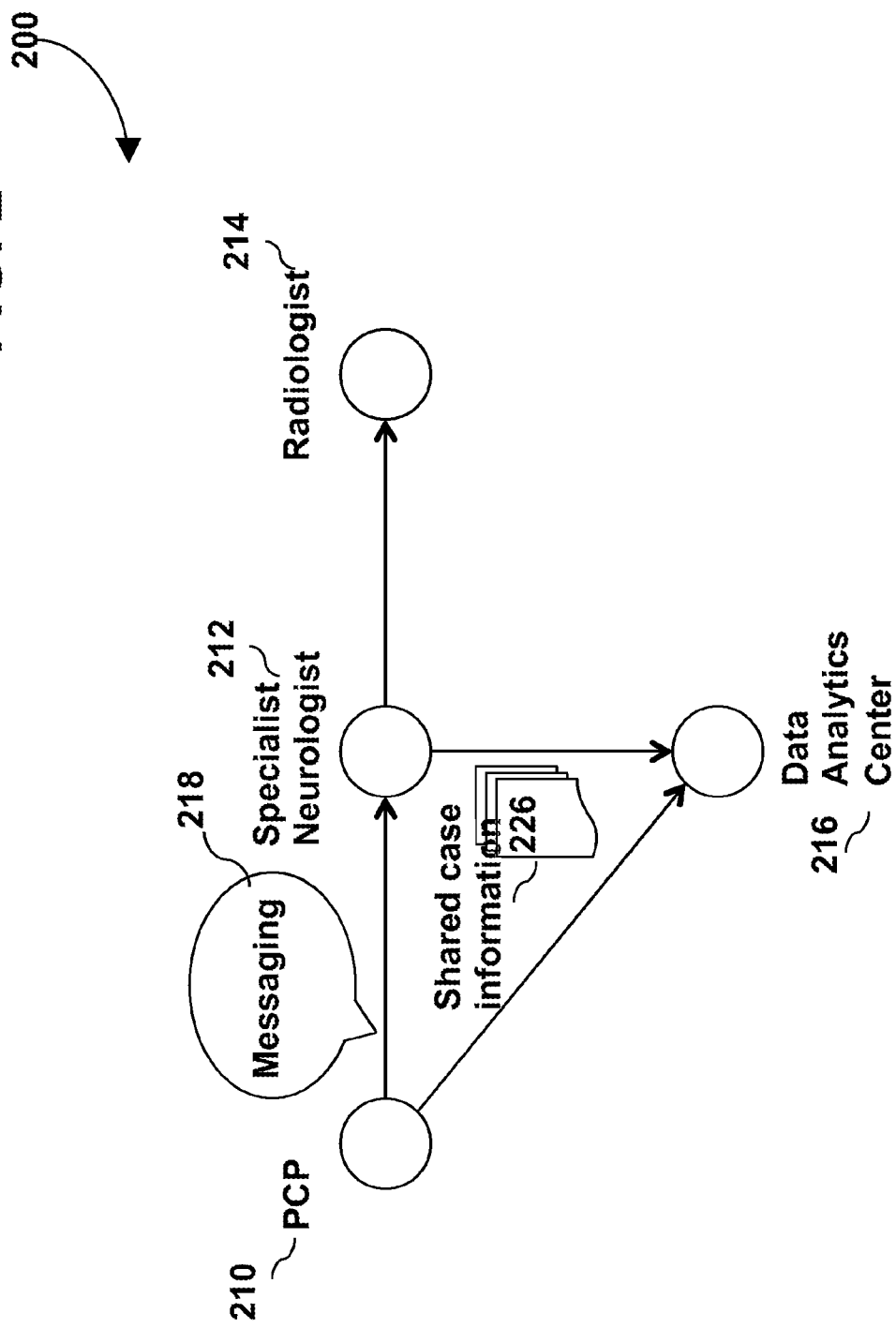
FIG. 2 is a diagram illustrating example data sharing of case information between participants of a social network for personalized medicine.

FIG. 2 is a diagram illustrating example data sharing of case information between participants of a social network 200 for personalized medicine, arranged in accordance with at least some embodiments described herein. In particular, FIG. 2 illustrates data sharing between a primary care physician (PCP) 210, a specialist neurologist 212, a radiologist 214, and a data analytics center 216. The participants of the social network 200 may further collaborate on shared case information 226, using message 218, for example.

Figure 3:
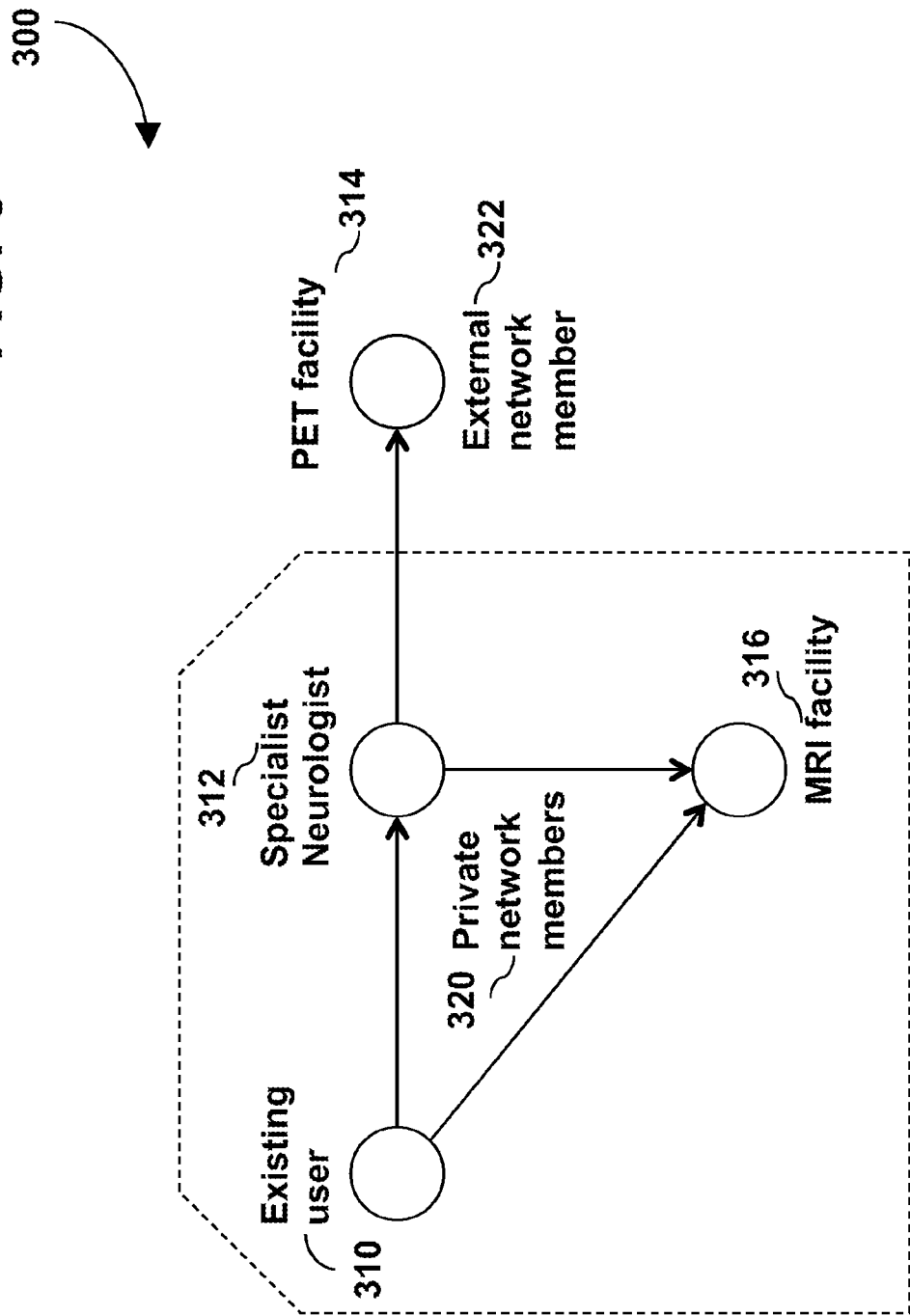
FIG. 3 is a diagram illustrating an example referral data flow between participants of a private network within a social network for personalized medicine.

FIG. 3 is a diagram illustrating an example referral data flow between participants of a private network 320 within a social network 300 for personalized medicine, arranged in accordance with at least some embodiments described herein. In particular, FIG. 3 illustrates the referral data flow between participants of the private network 320 that is part of the social network 300, such as within a hospital that includes an existing user 310, a specialist neurologist 312, and an MRI facility 316. FIG. 3 also illustrates an external network 322 that may be part of the social network 300. The external network 322 may include a PET facility 314 that is configured to share data with the participants of the private network 320.

Figure 4:
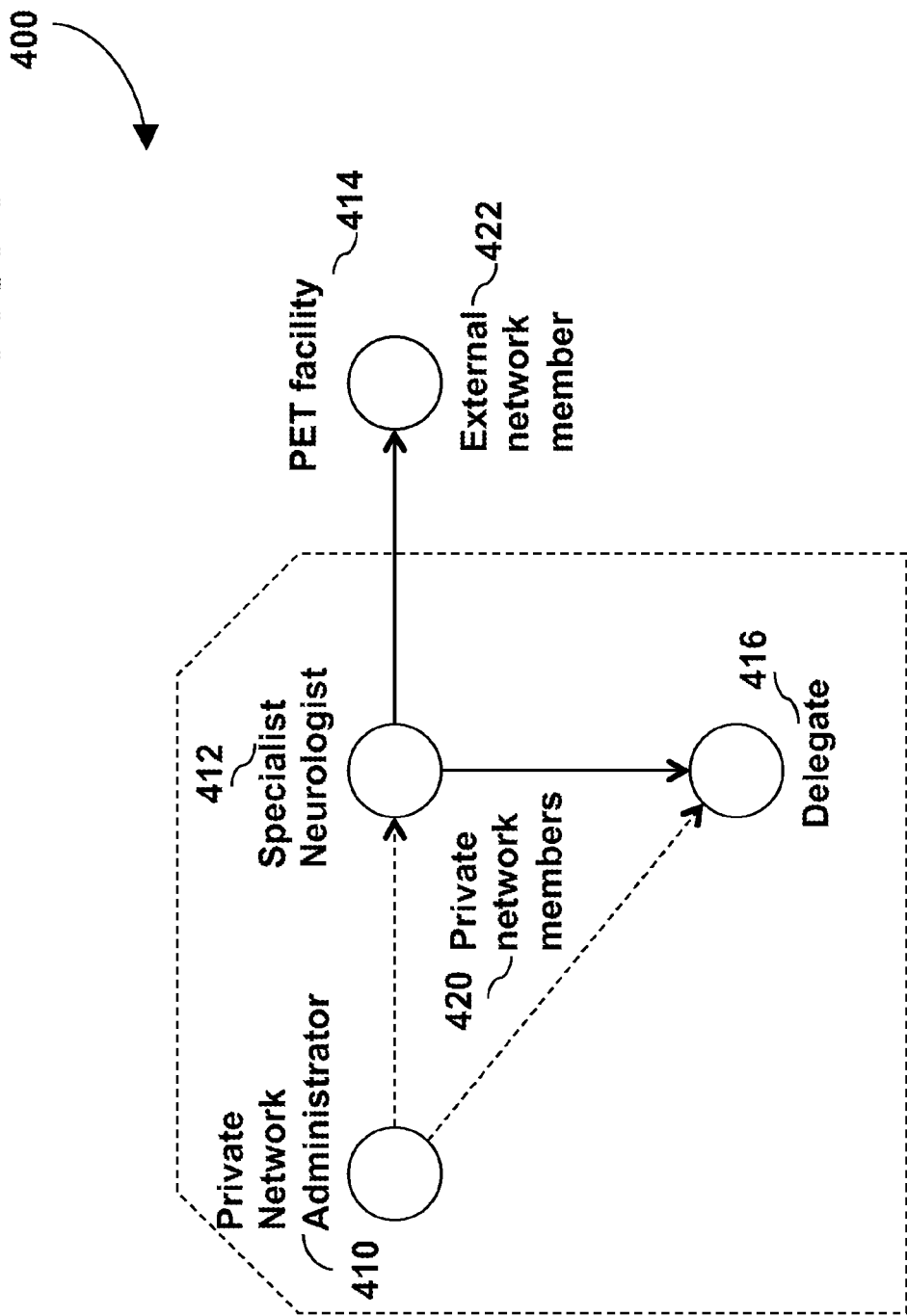
FIG. 4 is a diagram illustrating example network administration of a private network within a social network for personalized medicine.

FIG. 4 is a diagram illustrating example network administration of a private network 420 within a social network 400 for personalized medicine, arranged in accordance with at least some embodiments described herein. In particular, FIG. 4 illustrates network administration of the private network 420, such as within a hospital, through a private network administrator 410 that can add new private members and their delegates, such as a specialist neurologist 412 and a delegate 416. FIG. 4 also illustrates an external network 422 that may be part of the social network 400. The external network 422 may include a PET facility 414 that is configured to share data with the participants of the private network 420.

Figure 5:
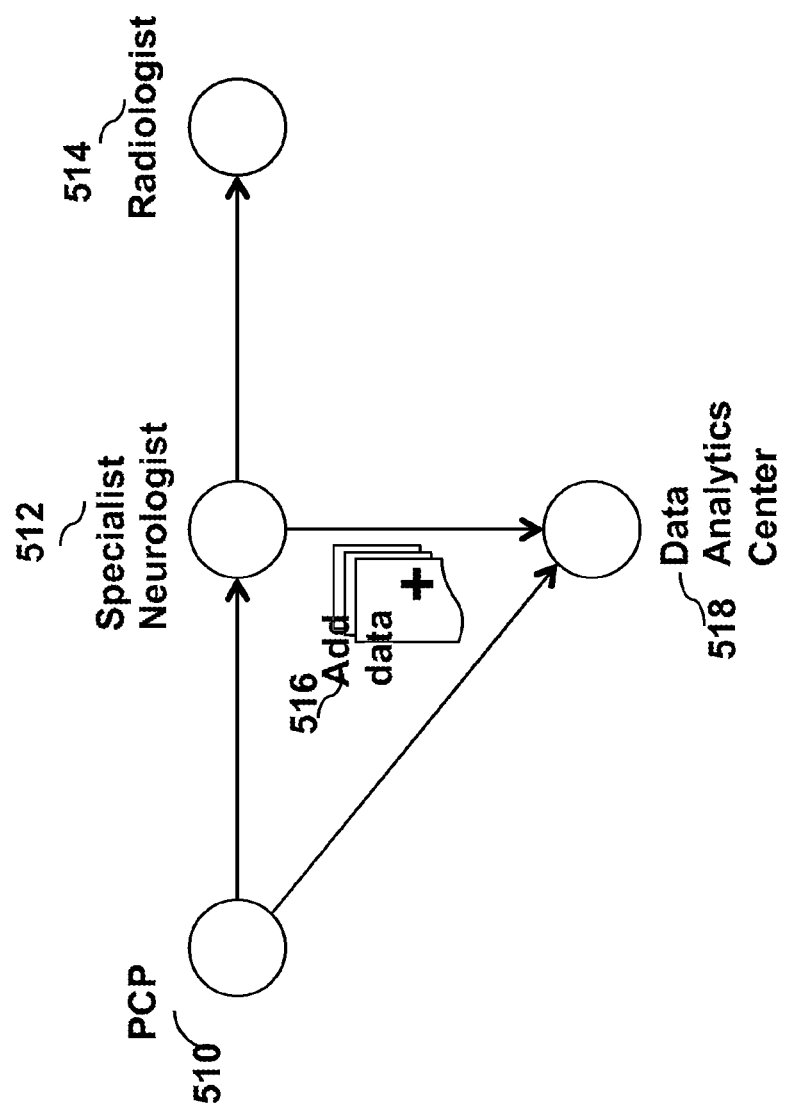
FIG. 5 is a diagram illustrating an example data flow of adding new information to a case within a social network for personalized medicine.

FIG. 5 is a diagram illustrating an example data flow of adding new information 516 to a case within a social network 500 for personalized medicine, arranged in accordance with at least some embodiments described herein. In particular, FIG. 5 illustrates information 516 being added by a specialist neurologist 512 that is associated with a PCP 510 and a radiologist 514 in the social network 500. The PCP 510 and/or the specialist neurologist 512 may further refer to/consult a data analytics center 518, to generate, for example, an integrated report concerning health care of the patient. The integrated report may be added to the case by the data analytics center 518.

Figure 6:
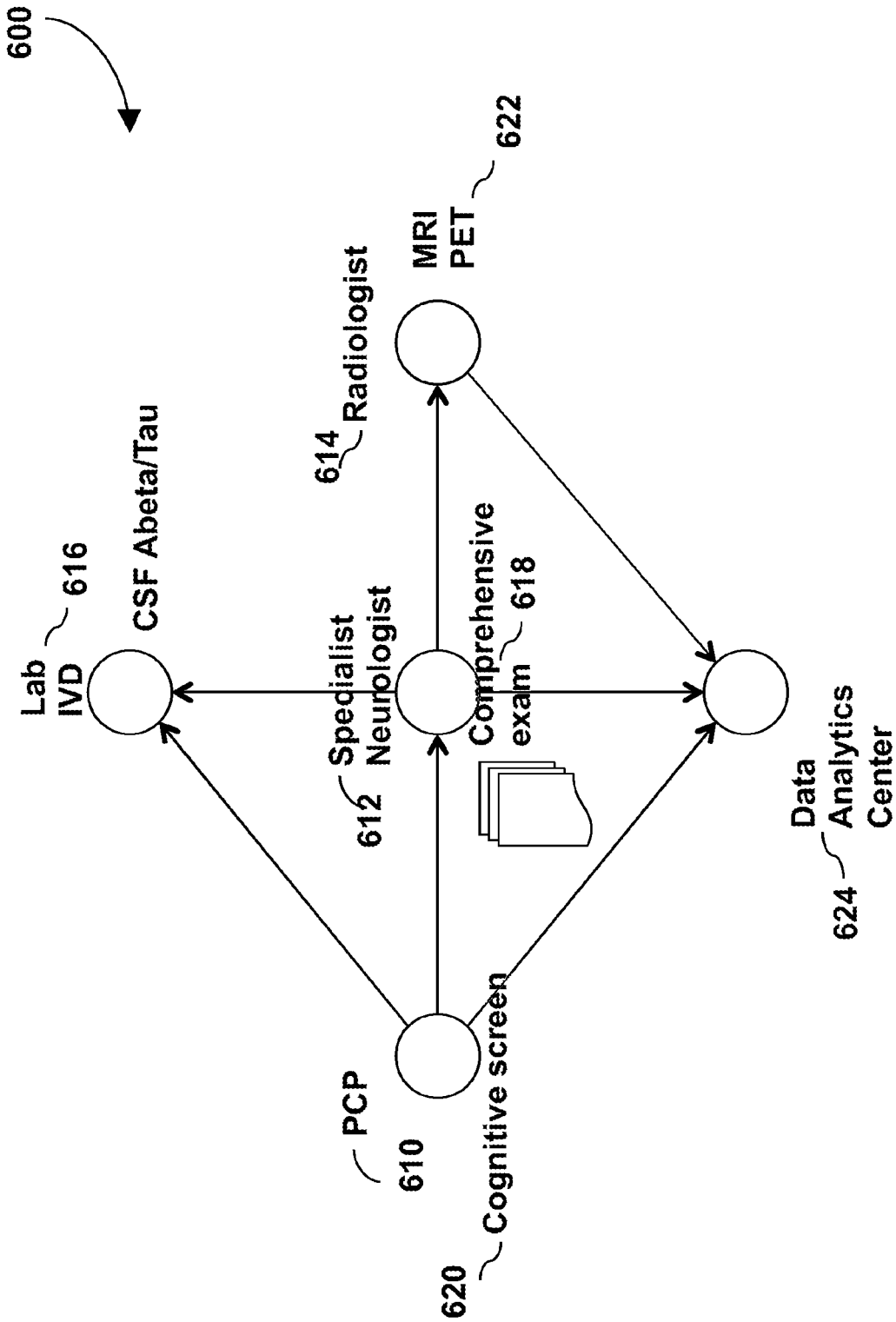
FIG. 6 is a diagram illustrating example diagnostic and therapeutic data flow within a social network for personalized medicine.

FIG. 6 is a diagram illustrating example diagnostic and therapeutic data flow within a social network 600 for personalized medicine, arranged in accordance with at least some embodiments described herein. In particular, the FIG. 6 illustrates the diagnostic and therapeutic data flow in the personalized medicine platform for Alzheimer's disease between the participants of the social network 600. For example, FIG. 6 illustrates that a PCP 610 may take a cognitive screen test 620 of a patient, which may include ordering an APOE testing and/or a blood screening test for Alzheimer's disease that is performed at a Lab 616. The PCP 610 may, after receiving the laboratory reports, consult a data analytics center 624, to consolidate the screening data into an integrated report. The PCP 610 may also refer the patient case to a specialist neurologist 612 for further evaluation of the patient. These step by the PCP 610 may conclude the screening episode of care for the patient. The specialist neurologist 612 may order another IVD test from the lab 616. The IVD test may entail CSF Abeta/Tau testing. The specialist neurologist 612 may further complete a comprehensive exam 618 on the patient that may, in some embodiments, include a full computerized cognitive battery. The specialist neurologist 612 may further refer/order a MRI and/or PET scan 622 from a radiologist 614, which may include image quantitation. The specialist neurologist 612 may then consult the data analytics center 624, to consolidate the comprehensive evaluation data into an integrated report. These steps by the specialist neurologist 612 may conclude a comprehensive diagnostics episode of care. In some embodiments, the data analytics center 624 may generate a predictive report for therapeutic stratification, as mentioned above, that may provide actionable information for the specialist neurologist 612, or the PCP 610 for prescribing a personalized drug for the patient related to Alzheimer's disease. In some embodiments, the PCP 610, may, augmented by the data analytics center 624, perform some or all of the functions of comprehensive evaluation as mentioned above and/or subsequent therapeutic stratification prior to prescribing the personalized drug.

Figure 7:
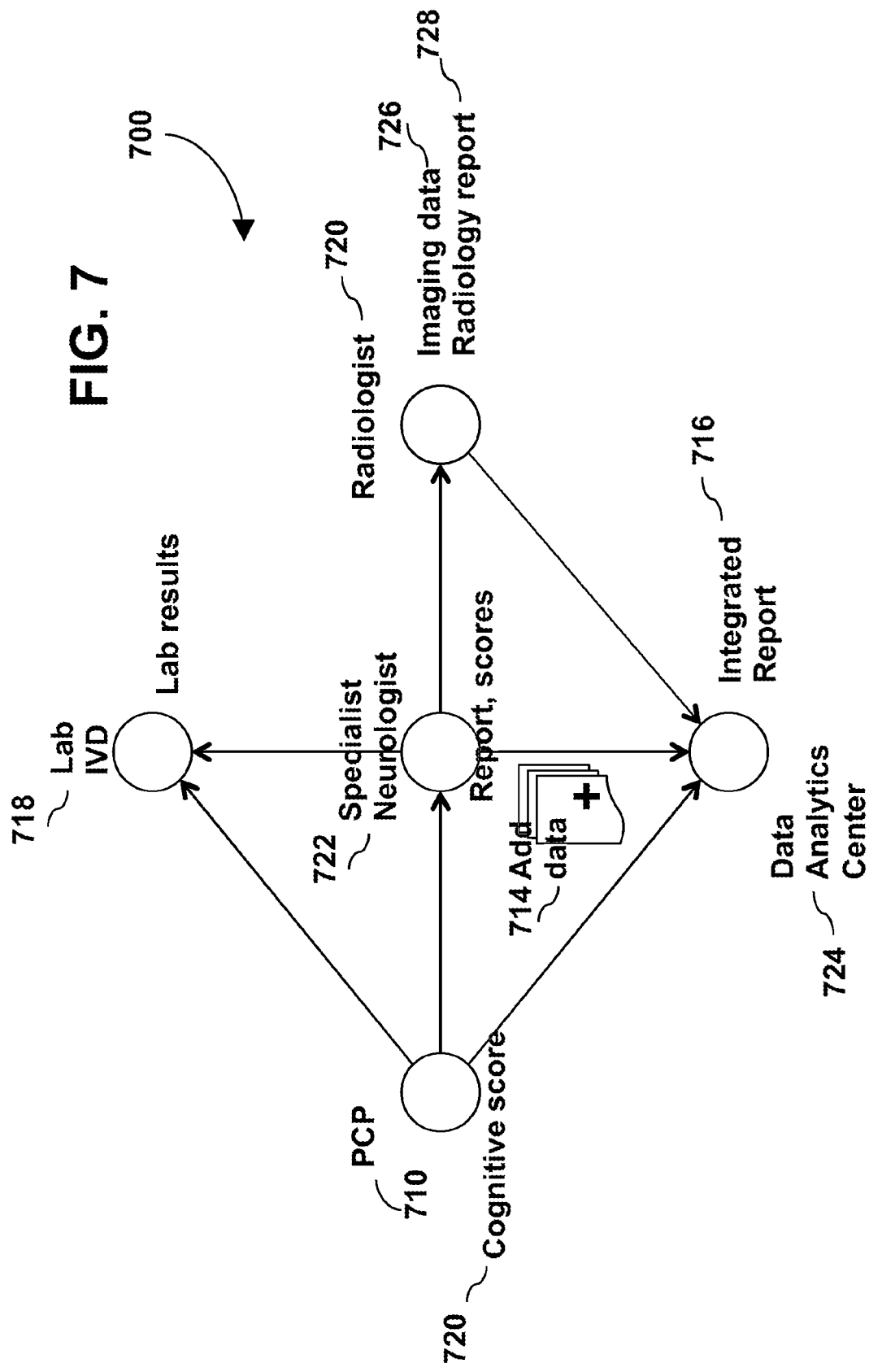
FIG. 7 is a diagram illustrating an example of adding and integration of case information within a social network for personalized medicine.

FIG. 7 is a diagram illustrating an example of adding and integration of case information within a social network 700 for personalized medicine, arranged in accordance with at least some embodiments described herein. In particular, FIG. 7 illustrates adding 714 the distinct components of information, for example, cognitive scores 720 from a cognitive screening test, ordered or performed by a PCP 710 to a data analytics center 724. In some embodiments, the cognitive scores 720 may further be complemented by an APOE testing and/or a blood screening test results which may be acquired from a lab 718. Other test results, for instance, imaging data 726 and/or a radiology report 728 may further be added to the case. Alternately or additionally, the data analytics center 724 may further add integrated reports 716 to the case.

Figure 8:
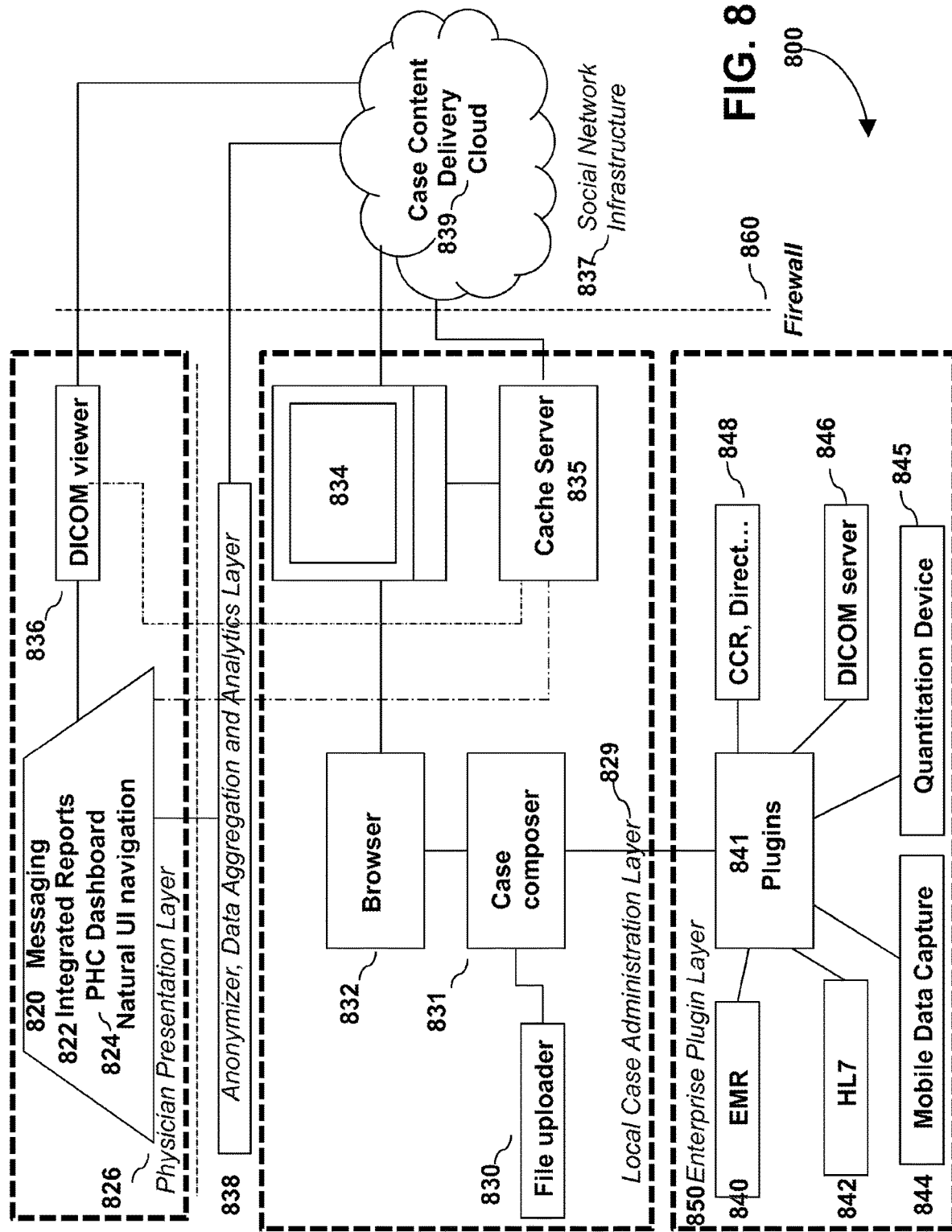
FIG. 8 is a diagram illustrating example components of a system that uses a social network for personalized medicine.

FIG. 8 is a diagram illustrating example components of a system 800 that uses a social network infrastructure 837 for personalized medicine, arranged in accordance with at least some embodiments described herein. The system 800 may include a social network infrastructure 837 that may interact with a local case administration layer 829, an anonymizer, data aggregation, and analytics layer 838, and a physician presentation layer 826. The social network infrastructure 837, in some embodiments, may be configured to allow for the interactions between the participants of social networks as described with respect to FIGS. 1-7.

The social network infrastructure 837 may include a scalable, cloud-based case content delivery network 839 that manages a HIPAA-compliant exchange of personal health information, including full audit trail, encrypted file transfer, and messaging between participants of a social network hosted by the social network infrastructure 837. The social network infrastructure 837 may further include system software, such as front-end (client) and server-side application software code, for example, web-enabled, or desktop virtualization application software components that may be used to implement the social network's core functionality. The social network infrastructure 837 may also include APIs for external applications to connect with the social network; application frameworks such as web and rich media application frameworks, database server software, and web server software; server virtualization software, load balancers, networking equipment, and server and storage equipment. The social network infrastructure 837 may include server equipment that may include diskless server nodes with solid-state drives (SSD). The social network infrastructure 837 may include storage equipment, which may include flash array storage. The social network infrastructure 837 may also include cloud-networking equipment such as low-latency network switches, and further include network security and encryption appliances.

The case content delivery cloud 839 may further be deployed in a private cloud infrastructure such as in a facility owned or rented by the social network operator, and/or a dedicated cloud facility with appropriate security implemented and managed by a third party. For example, the case content delivery cloud 839 may be hosted in a public cloud such as Amazon, or deployed in combination with a private cloud, for instance, in a hybrid cloud architecture with sensitive, non-anonymized information such as protected health information. In some embodiments, the case content delivery cloud 839 may further be deployed in a PaaS (platform as a service) environment, such as Force.com, that may eliminate complexities of managing the software and hardware infrastructure layers and automatically scaling the infrastructure as demand grows.

In some embodiments, the case content delivery cloud 839 may further be connected to specialized (such as for data transfer speed and certain viewers) third-party cloud-based repositories, for instance, image or genome sequencing data repositories, through the use of an API. In these and other embodiments, pointers such as URLs or XDS may be used to link content stored in the case content delivery cloud 839 to corresponding case content in the third-party repository.

The social network infrastructure 837 may be configured to communicate with the local case administration layer 829. The local case administration layer 829 may be configured to allow for local case administration by back-office personnel such as physician's assistants, nurses, or technicians may reside within the enterprise or health care provider's (such as hospital or practice) firewalls 860. Patient cases within the social network infrastructure 837, which may be cloud-based, may be accessed and managed through a device 834, such as a hospital desktop, laptop computer or mobile device via a web browser interface 832 (such as Firefox, Internet Explorer, Chrome, or Safari), or a non-browser based native application installed on the device 834, for example, an iOS, Android, Windows, or Mac OS software application. Case content, such as images or reports or other content, may be uploaded via a file uploader module 830 accessed by the case composer module 831. The case composer module 831 may provide functionality to enter a new patient, find an existing patient, or specify recipients for the case such as a specialist neurologist and/or data analytics center within the social network infrastructure 837. Case composer module 831 may further allow metadata, for instance, content describing information (such as category, description of files uploaded) to be added. Metadata may be imported directly from an EMR such as hospital EMR or cloud-based EMR 840. Case content may be organized in folders or directories. Actual case content may further be uploaded directly, such as images from a local DICOM server 846 (node) or cloud-based remote image repository. Similarly, case content can be downloaded onto a secured local device 834 such as for image viewing within a third party image viewer 836. A network administration module, as described earlier, may further allow generating a full HIPAA-compliant (and time-stamped) audit trail on all patient data within the social network infrastructure 837, for example, as to which user accessed certain patients.

In some embodiments, the local case administration layer 829 may include a locally installed cache server 835 that may be configured to replicate and/or prefetch content from the social network infrastructure 837 for faster access such as the third party image viewer 836. In some embodiments, an SSL connection may be established between cache server 835 and case content delivery cloud 839 to allow the cache server 835 to access information from the social network infrastructure 837. Similarly, content such as images may be batch uploaded using the cache server 835. The cache server 835 may be a software application locally installed on a local computer within the firewalls 860 of the hospital, or a network appliance, such as residing in a data center. The cache server 835 may be an embedded system appliance with flash memory, integrated firewall, and wireless networking capabilities. Alternately or additionally, the cache server 835 may be directly connected with physician interfacing applications and devices 834 such as tablets and wearable computing devices. Wearable computing devices may include, for example, eyeglasses with display capabilities.

In some embodiments, the cache server 835 may further be configured to encrypt or decrypt data stored on the cache server 835 prior to sending data to, or after receiving encrypted data from, the case content delivery cloud 839. In these and other embodiments, just encrypted data is stored in the case content delivery cloud 839 and could, for instance, be hosted in a public cloud.

In some embodiments, the local case administration layer 829 may be configured to communicate with the enterprise plugin layer 850. In particular, the case composer module 831 may be configured to communicate with or include plugins 841 that may be configured to provide interoperability between the local case administration layer 829 and other local health management systems within the health care provider's firewall 860. The other local health management systems may include EMRs 840, PACS 846, or other systems 842 supporting HL7 messaging protocols, such as laboratory information management systems (LIMS). The plugins 841 may allow import (or export) of data from/to such systems to the local case administration layer 829.

For example, the case composer module 831 may invoke a plugin application to connect with local EMR 840 to import case metadata for a given case. As another example, medical images may be imported into a case through the case composer module 831 after they are received from a local or cloud-based PACS 846. As another example, laboratory results may be imported into a case through the case composer module 831 after they are received from a LIMS via HL7 v2.x messaging. In some embodiments, the case composer module 831 may use the plugins 841 to access information from a personal health record (PHR) such as HealthVault. For example, the case composer module 831 may also use the plugins 841 to import via CCR (continuity of care) or Direct protocol 848 patient demographics, insurance information, medications, allergies, and care plan, among other information. In some embodiments, the plugins 841 may be pre-installed in the cache server 835.

In some embodiments, the plugins 841 may be configured to provide information to the case composer module 831 from mobile data capture devices 844. The mobile data capture devices 844 may include devices used for cognitive screen testing 620. In these and other embodiments, the case composer module 831 may connect directly with the mobile data capture devices 844 to a server device that stores the captured data, such as from a home-based screening device connected via the Internet. Similarly, a server device 845 may be used to run quantitative analysis on images, or on gene sequencing data, and export analysis data into the case using the case composer module 831. The server device 845 may further be a specialized or compact supercomputer for medical images analysis or NGS genome analysis, a NGS genome sequencing desktop device, or portable USB sequencing device. The server device 845 may also allow automatic backup of data within the social network interface 837 and/or function as a cache server 835, as described above.

The local case administration layer 829 and the social network infrastructure 837 may be further configured to communicate with a physician presentation layer 826. Physicians typically are time-constrained and require a different type of presentation layer than back-office personnel such as technicians or physician's assistants. To optimize delivery of information to a busy physician, various systems and applications may be utilized. For example, a mobile phone messaging app 820 or integrated reports 822 delivered through applications on mobile devices such as tablets or "phablets" may be used. Alternately or additionally, wearable display devices, such as intelligent wristbands/watches that may connect wirelessly with a patient's wristband/watch (for instance, with built-in cognitive self-test or continuous monitoring application), and invoke presentation of a patient's integrated report within the intelligent wristband/watches. In this manner, a physician may receive information about a patient when the patient arrives to see the physician.

In some embodiments, the physician presentation layer 826 may include an interactive dashboard 824 tailored for personalized health care (PHC) that may use touch, voice, or other natural user interface (NUI) as inputs. The interactive dashboards 824 may be displayed on flexible or disposable display devices folded into drug packaging materials. Alternately or additionally, the interactive dashboards 824 may be displayed on wall-mounted TVs that may wirelessly connect with a patient's wearable computer wristband/watch and thereby invoke presentation of the patient's information to the physician. Interactive dashboards 824 may further be projected by a wirelessly-connected projector device against the walls of a treatment room or doctor's suite.

Image viewing capabilities, such as from a third part image viewer 836, such as a DICOM viewer, may be integrated into dashboards, integrated reports, or run as browser-based or standalone applications. In these and other embodiments, images may be downloaded onto a device, such as the device 834, for image review purposes or imported into a local or remote PACS system 846. In some embodiments, image viewing functionality may not require that the actual images be downloaded onto a device. In these and other embodiments, application components may transmit pixel data that may be rendered onto the device display, while the actual image files reside on a local server, such as the cache server 835 or on a remote server, such as a server within the social network infrastructure 837. In some embodiments, to render images without downloading the images, the physician presentation layer 826 may utilize the HTML5 web standard, Java, or desktop virtualization technologies.

The physician presentation layer 826, the social network infrastructure 837, and the local case administration layer 829 may be configured to communicate with an anonymizer, data aggregation, and analytics layer 838. The anonymizer, data aggregation, and analytics layer 838 may include one or more sub-systems that provide functionality to de-identify patient data, and store such de-identified data in a centralized or federated repository for further analysis, such as advanced "big data" analytics. For example, the anonymizer, data aggregation, and analytics layer 838 may include an anonymizer sub-system, a data aggregation sub-system, and/or an analytics sub-system.

In some embodiments, the anonymizer sub-system that performs the de-identifying of patient data may be a server component installed inside the local case administration layer 829. The data aggregation sub-system may consist of a large-scale and/or distributed database and file storage system, installed on premises, or in an external facility, for instance, at a cloud services provider such as Amazon.

The analytics sub-system may consist of a server-based system, such as a compute node or plurality thereof, that are configured to run application software for automated quantitation of images, such as hippocampal volume measurements. The analytics sub-system may further be cloud-based, such as a private cloud-based compute resource and connected to the social network infrastructure 837 or other third party infrastructures discussed herein. The analytics sub-system may further consist of an advanced, automated analytics system and, as described earlier, such as installed in a data center, cloud-computing resource such as Amazon EC2, or a "data center in the cloud." The advanced automated analytics subsystem may run analytics against the aggregated data and be in close proximity thereof, for instance, in the same facility.

The system 800 illustrated in FIG. 8 may be used for the electronic delivery of information in personalized medicine and Alzheimer's disease (AD) diagnostics. The system 800 may perform the electronic delivery of information by utilizing a scalable cloud-based social network architecture to capture multiple patient data streams and then route such information between various health care providers. The system also includes a data analytics center (such as a fully automated "big data analytics" system component) that analyzes the data and presents the information in distilled and "curated" form to a prescriber (for instance, on mobile devices). The system 800 is applicable to any personalized health care application and therapy area, for example, neurodegenerative diseases, multiple sclerosis, and cancer, among others.

The system 800 is, without limitation, particularly well-suited in the context of biologics drug therapies that warrant personalization for risk/benefit and economic considerations. The system 800 is further well-suited to connect with mobile/wireless sensors that acquire real time and continuous data streams. The system 800 is further well-suited for using imaging and/or next-generation sequencing data which may require data analytics prior to using the imaging and/or next-generation sequencing data for personalizing health care in a real-world clinical application context outside academic research. The system 800 may further be implemented in computer software, or in hardware circuitry, or any combination of software and hardware components, and is not limited to any specific software or hardware implementation.

FIG. 8 illustrates some of the major components of a system described herein and the data flow for providing personalized medicine. In some embodiments, a service provider/operator may implement components 837, 839, 838, 820, 822, 824, 830, 831, 835, 831, 841, 844, and 845, of the system 800, and provision services and devices to certain users and/or members of the social network infrastructure 837 on an on-demand, subscription, and/or pay-per-use basis, or other monetization basis such as fee-based, advertising supported, or on "freemium" basis. The members may include physicians, back-office personnel, such as physician assistants or nurses, and may control and own certain devices and software 826, 834, 832, and 860 to access the implemented components 837, 839, 838, 820, 822, 824, 830, 836, 835, 831, 841, 844, 845, for instance, and to securely upload protected health information from hospital or external repositories 840, 842, 846, and 848.

In some embodiments, the case content delivery cloud 839 component of social network infrastructure 837 may be implemented as a web-based system using a number of common web technologies such as AJAX, LAMP stack, Java, Javascript, XML/XSLT, Python, web application frameworks such as Ruby, ASP.NET, and/or other proprietary frameworks, server libraries, and GUI components that enable rapid development of custom, AJAX-enabled cross-browser applications. Web services may further be implemented via RESTful APIs, which may include open-source SMART API, to drive interactive reports 822 and interactive dashboards 824; or APIs to drive third-party natural interface (NUI) devices, for example, augmented-reality eyeglasses. In some embodiments, native applications may be installed within the physician presentation layer 826, or local case administration layer 829 (such as on the device 834), that connect securely via the Internet to a back-end component of the case content delivery cloud 839 system. Such security may include security via 256-bit, 512-bit, 1024-bit AES SSL, or higher bit strength encryptions that may be implemented for secure Internet communications, or by implementing other protocols, for example, transport layer protocol (TSL).

In some embodiments, native mobile applications within the physician presentation layer 826 may, for instance, be developed using mobile development tools such as Android or iOS SDK, Corona SDK, Sencha, or Unity, among others. Other development tools may further be used to implement certain native interactive charting/reporting functionality for integrated reports 822 and interactive dashboards 824, as described earlier, and third party SDKs for wearable computing devices. Other development tools may further be used to implement other types of NUI devices such as gesture-based controllers, for example, Kinect, or LeapMotion, among others.

Access control to the social network infrastructure 837 and/or applications within the physician presentation layer 826 may, for example, be implemented using a web-based login page (with encrypted password submission), single sign-on (SSO) approaches (such as LDAP, Active Directory, OpenSSO), or biometric SSO. Biometric identity verification may further include one or more biometric factors, for example, gesture, hand shape, EEG, eye tracking, retina signatures, fingerprint, speech, face recognition, and/or other biometric features captured from an access device. Access control may further be implemented using certain SDKs/APIs or other electronic access control approaches, for example, a card-based approach or a smartphone equipped with electronic identity verification.

In some embodiments, the case composer module 831 may be embodied in a web-based application, such as Javascript. In some embodiments, the file uploader module 830 may be implemented in Java or Flash. In some embodiments, the front-end (client) applications on devices in the local case administration layer 829 (such as on the device 834), or on a desktop computer in the physician presentation layer 826 may be implemented using integrated development environments (IDEs) such as Visual Studio, Xcode, Eclipse, and other software development environments. DICOM viewing may further be integrated using OsiriX.

The various plugins 841 for bidirectional (import/export) interoperability with other systems, for instance, hospital, external, or locally-installed instruments/appliances or other embodiments within the enterprise plugin layer 850 may be embodied as a native desktop or server application or Java application. Alternately or additionally, the various plugins 841 may be implemented using an IDE, such as the IDE previously mentioned. Open source interface engines, for instance, Mirth Connect and/or SMART API, may further be used to implement said plugins to hospital or external repositories such as HL7, CDA, DICOM, and/or from PHRs via CCR/Direct protocol. The various plugins 841 may further be embedded pre-installed in the above-mentioned instruments such as NGS sequencing devices, specialized devices supporting local-quantitative medical images analysis, and backup to the social network infrastructure 837. The various plugins 841 may further be embedded pre-installed in the cache server 835.

In some embodiments, the cache server 835 may be implemented as a software application and installed on a local computer within the hospital's firewalls or on a server residing in a data center. The cache server 835 may further be implemented in embedded system code, for instance, running under Embedded Linux distributions (for example, OpenWrt) or real-time operating system (RTOS) such as VxWorks or Neutrino. In some embodiments, the cache server application code may be implemented using IDEs such as Eclipse, Tornado, QNX, Visual Studio, Xcode, and other software development tools. The cache server 835 may further encrypt or decrypt data stored on the cache server 835, prior to sending data to, or after receiving encrypted data from case content delivery cloud 839. In these and other embodiments, encrypted data is stored in the case content delivery cloud 839, and could, for instance, be hosted in a public cloud. Encryption may, for instance, be implemented via FUSE-based EncFS encrypted file system in Linux or TrueCrypt for other operating systems.

The cache server 835 may, in some embodiments, have a very compact form factor and designed for small-size physician practices. For example, the cache server 835 may include a turnkey-embedded system appliance with flash memory and wireless networking capabilities, for instance Bluetooth, NFC, or Wi-Fi. In these and other embodiments, the cache server 835 may further incorporate integrated firewall and network intrusion detection capabilities.

In some embodiments, the cache server 835 may wirelessly connect with physician-interfacing applications and devices within the physician presentation layer 826 such as tablets and wearable computing devices, for example, smart eyeglasses with built-in displays and/or have circuitry components to drive other types of natural user interfaces, such as gesture-controlled interfaces. The cache server 835 may be implemented using an RTOS, such as VxWorks, or a secure embedded Linux distribution to ensure high stability and security.

The anonymizer, data aggregation, and analytics layer 838 may be embodied in an analytic data center and comprised of sub-systems that provide functionality, as described earlier, to de-identify patient data and store such de-identified data in a centralized or federated repository for further analysis. The system 800 may include one or multiple of the analytic data centers. In some embodiments, the analytic data center may be tailored to the needs of certain customers, such as proprietary reference data from a pharmaceutical company, health system, payor, or public-private partnership. The tailored analytic data center may be run, for example, in a private cloud setting.

An anonymizer sub-system within the analytic data center may be a server component installed inside the firewall of the analytic data center. Anonymizer may be implemented with third party or open source data anonymization software tools, such as XNAT for DICOM data, Mirth Connect for HL7 data, and/or custom Python shell scripts may be written to strip off protected health information such as patient identifying information.

In some embodiments, data formats of data in the analytic data center may be standardized before further analysis, for instance, to quantitative information, in favor of qualitative data. In these and other embodiments, curation of the data may be fully automated for the standardized data types. In some embodiments, the quality control and anonymization of data imported into case content delivery cloud 839 may further be embodied in one or more plugins of the various plugins 841, such as mobile data capture devices 844 and server device 845 plugins. For example, these plugins may be developed with open source software components such as RSNA CTP. The plugins with quality-control (such as for correct image acquisition parameters in a DICOM header) and anonymization functionality, may further be complemented by Python shell scripts implemented on a server in the analytic data center and may check image data for defects and reject defective images prior to storing/aggregating such data.

Non-imaging and/or non-sequencing data may be stored in a SQL (such as MySQL) or NoSQL database (such as Cassandra, MongoDB, or Hbase), and/or Hive, while media-rich contents such as imaging or NGS source data may be stored in file systems, for example, distributed HDFS for performance reasons. The case content delivery cloud 839 may support semantic data integration to interrelate with data from other databases and datasets, for instance, ADNI or ConnectomeDB. Image files may further reside in an external cloud image repository optimized for performance and referred to by a URL link or other pointer stored in the case content delivery cloud 839, or via APIs such as RESTful APIs.

The analytics sub-system within the analytic data center may be embodied in a server-based system inside the firewall of the analytic data center, such as a compute node or plurality thereof. The analytics sub-system may be configured to run application software for automated quantitation of images, for example, hippocampal volume measurements and/or quantitation of other brain structures using MRI, voxel-based amyloid PET quantitation, texture analysis of MRI scans, or brain "connectome" analysis based on DTI fiber tracking, and fMRI. Automated quantitation may, for example, be implemented in MATLAB computer code and compiled as executable or C/C++ shared library, as part of an automatic quantitation server code. In some embodiments, the server code for the analytics sub-system may further be parallelized. In some embodiments, automatic quantitation code within the analytics sub-system may further exhibit certain numerical instabilities of calculations, which may be caused by the high temperature of a computer chip, cosmic radiation, moisture, and/or manufacturing defects. The automated quantitation code may further correct for such numerical instabilities by incorporating external real-time data, such as sensor data in the calculation, and/or including re-calculations on another computer chip to flag calculation errors based on the chip manufacturing defects. Such calculation errors may further be detected by running random check calculations on external reference datasets, for example, imaging data in the ADNI or other databases, and comparing the random check calculations from external reference datasets against manually-traced volumes in such database. The automated quantitation code may further store a physical hardware signature of the compute node on which code is running on. For example, dmidecode in Linux may be used to obtain detailed information of the chip used in performing the calculation; said hardware signature may then be compared against external hardware reference data, to flag potential calculation errors due to hardware used in certain circumstances, and, given said external sensor data, may then allow correction by performing a recalculation at a later time/on different hardware.

In some embodiments, the analytics sub-system may be configured to perform connectome analysis, which may be based on data from ultra-high resolution DTI MRI or resting-state fMRI.

In some embodiments, the analytics sub-system may further include so-called "social network analysis" (SNA) tools that may be implemented using open source tools such as Cytoscape and R tools for SNA. The SNA tools, in one particular embodiment, may be utilized to perform brain connectome analysis. In another embodiment, SNA tools may be used to perform analysis on the social network infrastructure 837. For example, the SNA tools may perform analysis on the social network infrastructure 837 to discover certain patterns of user interaction between the participants of the network and improve services offered to the participants. Alternately or additionally, the SNA tools may perform analysis on the social network infrastructure 837 to provide insights to payors to optimize delivery of health care in a cost-effective way. The SNA tools for brain connectome analysis may, in yet another embodiment, incorporate other graph theory analysis tools, for instance, Brain Connectivity Toolbox (BCT) or MatlabBGL. The Brain Connectivity Toolbox (BCT) may, for example, be used to calculate "small-world network" indexes and properties of patients suspected of having Alzheimer's disease. The Brain Connectivity Toolbox (BCT), in another embodiment, may further be used for visualization to aid data scientists or physicians using interfaces in the physician presentation layer 826, such as Brainnet Viewer, Connectome Viewer Toolkit, or topological graph theory visualization tools.

In some embodiments, the analytics sub-system may, in another embodiment, run application software to perform automated "big data" analytics, as described earlier. The automated analytics may run analytics for data of a patient against aggregated data of multiple patients, for example a large number of patients. The analytics sub-system may be embodied in an analytic data center, cloud-computing resource such as Amazon EC2, Google Compute Engine, Azure, or an analytic data center in the social network infrastructure 837.

In some embodiments, the analytics subsystem may further be in close proximity to the aggregated data, for instance, in the same facility. In some embodiments, the analytics subsystem may provide in-memory analytics with the analyzed large-scale (e.g., terabyte-order or higher) data residing in memory. The in-memory analytics may reduce latency and provide instant analytics. In some embodiments, the analytics subsystem may further be accessed by physician applications and devices 826 and 836, as described earlier. In these and other embodiments, a first analytics server, for instance, an in-memory analytics server, may be used to render certain interface components to or physicians in the physician presentation layer 826, or to data scientists. A second web server may be used for interface components that may be rendered. Alternatively or additionally, desktop virtualization techniques may be used for rendering interface components (for instance, Citrix, or open source alternatives).

In some embodiments, the analytics system may implement machine learning or other data mining techniques, for example, natural language processing, neural networks, Support Vector Machines (SVM), and statistical classifiers such as k-Nearest Neighbor (k-NN), or Linear Discriminant Analysis (LDA). The data mining techniques may be implemented using, for example, NLTK, R, or MATLAB, PLINK, or by using the Apache Mahout machine-learning library, which is built on top of the Hadoop system and may be highly scalable.

In some embodiments, a physician may request analytics to predict treatment response, future onset of disease, or calculate a probability of current disease given a certain combination, among other things, in a pre-symptomatic Alzheimer's disease (AD) patient. The analytics in these and other embodiments may be based on a biomarker pattern combination of the patient. The machine learning algorithms, for instance, a supervised neural network or SVM classifier, may be trained on aggregated data from multiple other patients. The trained algorithm may then be applied to the patient's biomarker combination. The trained algorithm may further be trained to estimate Bayesian a posteriori probabilities, to estimate the probability of disease with a given set of biomarkers based on known conversion to AD status from aggregated longitudinal data.

A physician, through the physician presentation layer 826, may also invoke further analytics. The further analytics may include the identification of useful add-on markers by calculating predictive power of the add-on markers, for example, by calculating area under the receiver operating characteristic (ROC) curve or AUC values of the proposed biomarker combination from the aggregated data. The identification of useful add-on markers may be performed by running a simulation of adding default (e.g., mean) values for the new biomarkers. Based on the simulations, the analytics system may calculate a revised Bayesian a-posteriori probabilities, with the add-on markers in order to estimate the potential gain in diagnostic certainty. Certain statistical classifiers may further use a priori (prior) probability of disease as model input, which could, in another embodiment, be estimated based on risk factors and epidemiological data, such as cardiovascular risk factors and age, when these variables are not included directly as input variables.

Figure 9:
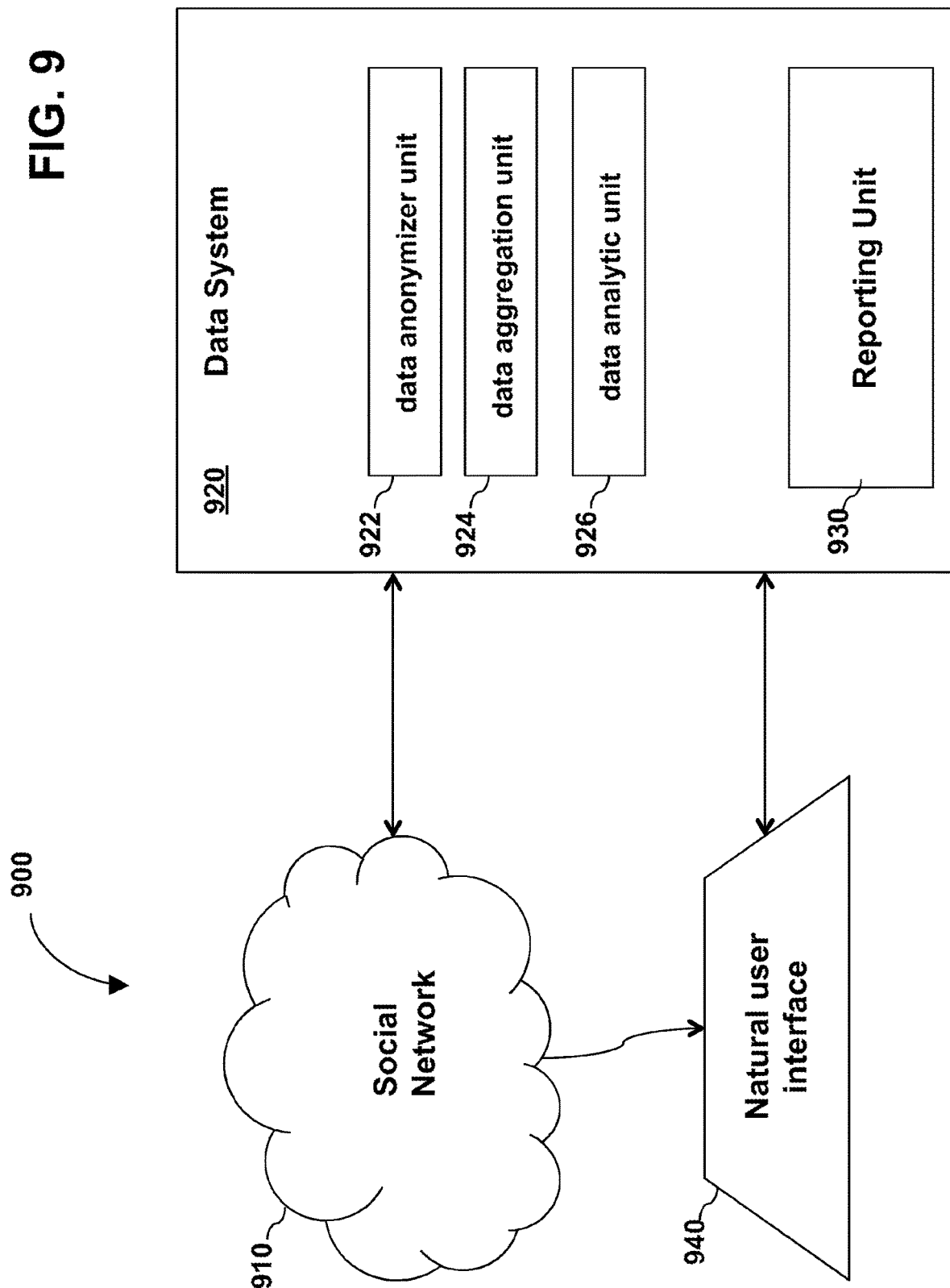
FIG. 9 is a diagram illustrating an example system for personalized medicine.

FIG. 9 is a diagram illustrating an example system 900 for personalized medicine, arranged in accordance with at least some embodiments described herein. The system 900 may include social network 910, a data system 920, and a natural user interface (NUI) unit 940 that may be communicatively coupled and allowed to exchange information therebetween.

The social network 910 may be configured analogous to the social network 100 of FIG. 1. Alternately or additionally, the social network 910 may be analogous to the social network infrastructure 837 of FIG. 8. In some embodiments, the social network 910 may be configured to facilitate interactions between multiple participants with respect to health care diagnostics of a patient. In some embodiments, the data system 920 may be included in the social network 910 or outside of the social network 910. The social network 910 may store patient data, such as biomarkers from images and other tests performed on or by one or more patients. In some embodiments, the patient data may be imported via the natural user interface unit 940 or some other interface.

The natural user interface unit 940 may be analogous to the physician presentation layer 826 of FIG. 8, and may be configured to send data to and receive data from the social network 910 and the data system 920. Additionally, the natural user interface unit 940 may be configured to interact with a physician associated with the patient. The natural user interface unit 940 may receive instructions from and present information to the physician. In some embodiments, the natural user interface may be further configured to instruct the data system to analyze data based on an instruction from the physician.

The data system 920 may include various units, including a data anonymizer unit 922, a data aggregation unit 924, a data analytics unit 926, and a reporting unit 930. In some embodiments, the data system 920 may be analogous to analytic data centers discussed herein.

The data anonymizer unit 922 may be configured to receive patient data associated with the health care diagnostics of a patient and to remove at least a portion of patient identifying information from the received patient data to generate first anonymized data. The data anonymizer unit 922 may be analogous to the anonymizer sub-system discussed with respect to FIG. 8. In some embodiments, the patient data being sent to the social network 910 via the natural user interface unit 940 may be received by the data anonymizer unit 922 first and a portion of the patient identifying information may be removed. In some embodiments, patient data in the social network 910 may be sent to the data anonymizer unit 922 and the patient identifying information may be removed from the patient data. The patient data may then be sent back to the social network 910.

The data aggregation unit 924 may be configured to store the anonymized patient data and to store anonymized data of at least one other patient.

The data analytics unit 926 may be configured to analyze the patient data using other patient data from within the social network 910, in particular from data aggregation unit 924. For example, in some embodiments, the patient data may include biomarkers. By analyzing the biomarkers of the patient data in relation to biomarkers from data from other patients or healthy individuals, information concerning the patient may be determined. The information may relate to diagnosis of a disease, therapy of a disease, and/or progression of a diagnosed disease, among other things. In some embodiments, the data analytics unit 926 may be configured to curate the patient data and/or information determined by the data analytics unit 926. The data anonymizer unit 922 may be analogous to the analytics sub-system discussed with respect to FIG. 8.

The reporting unit 930 may be configured to receive information and the patient anonymized data in order to generate a report that may be presented to the physician through the natural user interface unit 940.

Modifications, additions, or omissions may be made to the system 900 without departing from the scope of the present disclosure. For example, the system 900 may include other modules, units, or systems than those described above. Furthermore, the social network 910 may include various other aspects than those described above.

Figure 10:
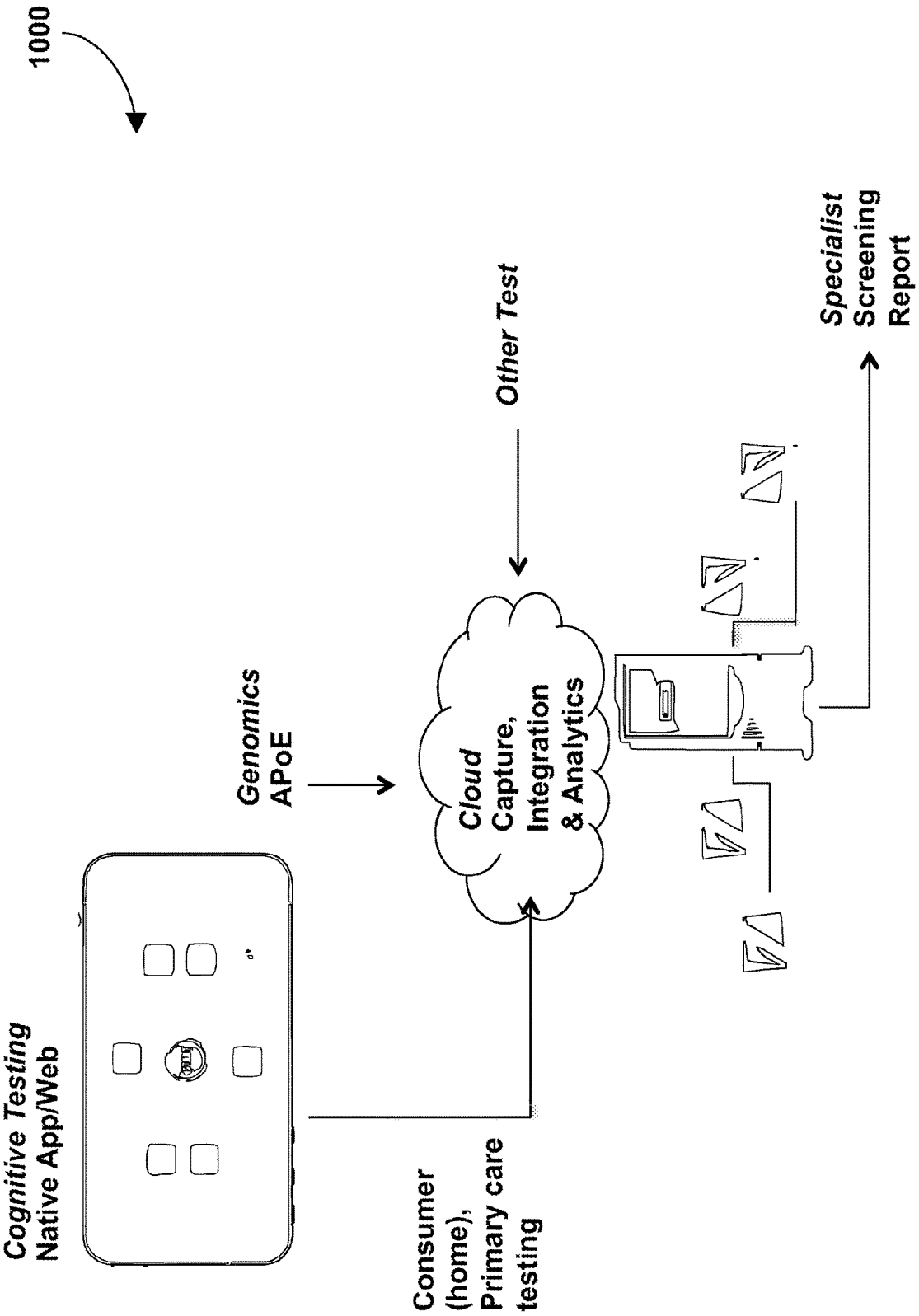
FIGS. 10-14 are data flows for example methods of generating reports for presentation.

FIG. 10 is an example data flow of an example method 1000 of generating a report for presentation, arranged in accordance with at least some embodiments described herein. For example, in the method 1000, an integrated screening report may be generated from a low-cost screen for early Alzheimer's disease (AD), such as prodromal AD. The report may consist of a patient completing the low-cost screen, such as a cognitive test, on a mobile device at the patient's home or at a primary care physician's office. In some embodiments, the cognitive test may be administered using a web-based application, such as an HTML5 web application or using a native app on a mobile device or some other computing device.

After completing the cognitive test, when the patient receives a score above a threshold that indicates a likelihood of AD, additional tests may be ordered and/or taken by the patient. For example, the patient may undergo a genetic test for an APOE genotype and/or testing for certain genetic variations, such as single-nucleotide polymorphisms (SNPs). SNPs may further be selected from a list generated by a quantitative trait locus genome wide association analysis (QTL GWAS). Alternately or additionally, the patient may undergo in-vitro diagnostics (IVD) screening tests such as a blood test or an eye-based screening test configured for detecting the presence of ocular deposits of amyloid beta peptide. The patient may undergo other tests as well, such as emerging screening tests that may include continuous wireless monitoring by gait sensors, eye tracking, or wireless sleep monitors such as accelerometers and/or electroencephalogram (EEG) sensors, etc.

In some embodiments, the patient or primary care physician of the patient may order the additional tests. In some embodiments, the additional tests may be ordered directly through the cognitive testing application. For instance, the patient may press an order button on the web-based application or receive a coupon from an in-app purchase. In some embodiments, the additional tests may be performed by a personal genome service's online store, such as 23andMe. Alternately, the patient may already have an account with the personal genome service and log into the account to retrieve the patient's genetic data through an application-programming interface and import the data into a social network cloud, such as the case content delivery cloud 839 of FIG. 8.

The data from the additional test may be captured in a social network cloud and combined with the data from the cognitive test. The combined data from the patient may be analyzed and curated in a concise, summarized form, as described above. For example, the combined data may be curated into a report, such as an integrated screening report. The integrated screening report may suggest a comprehensive diagnostic evaluation. Alternately or additionally, the integrated screening report may not suggest a comprehensive diagnostic evaluation. Whether the integrated screening report suggests a comprehensive diagnostic evaluation may be based on whether the combined data suggest the likelihood of AD being above a threshold. In some embodiments, the combined data may be compared or analyzed with respect to other data of other patients that may or may not have been diagnosed with AD. This analysis may assist in determining when the combined data may indicate a likelihood of AD.

When the report indicates a likelihood of AD or otherwise indicates that a comprehensive diagnostic evaluation should be performed, a primary care physician of the patient may send to/share with a specialist in the social network.

Figure 11:
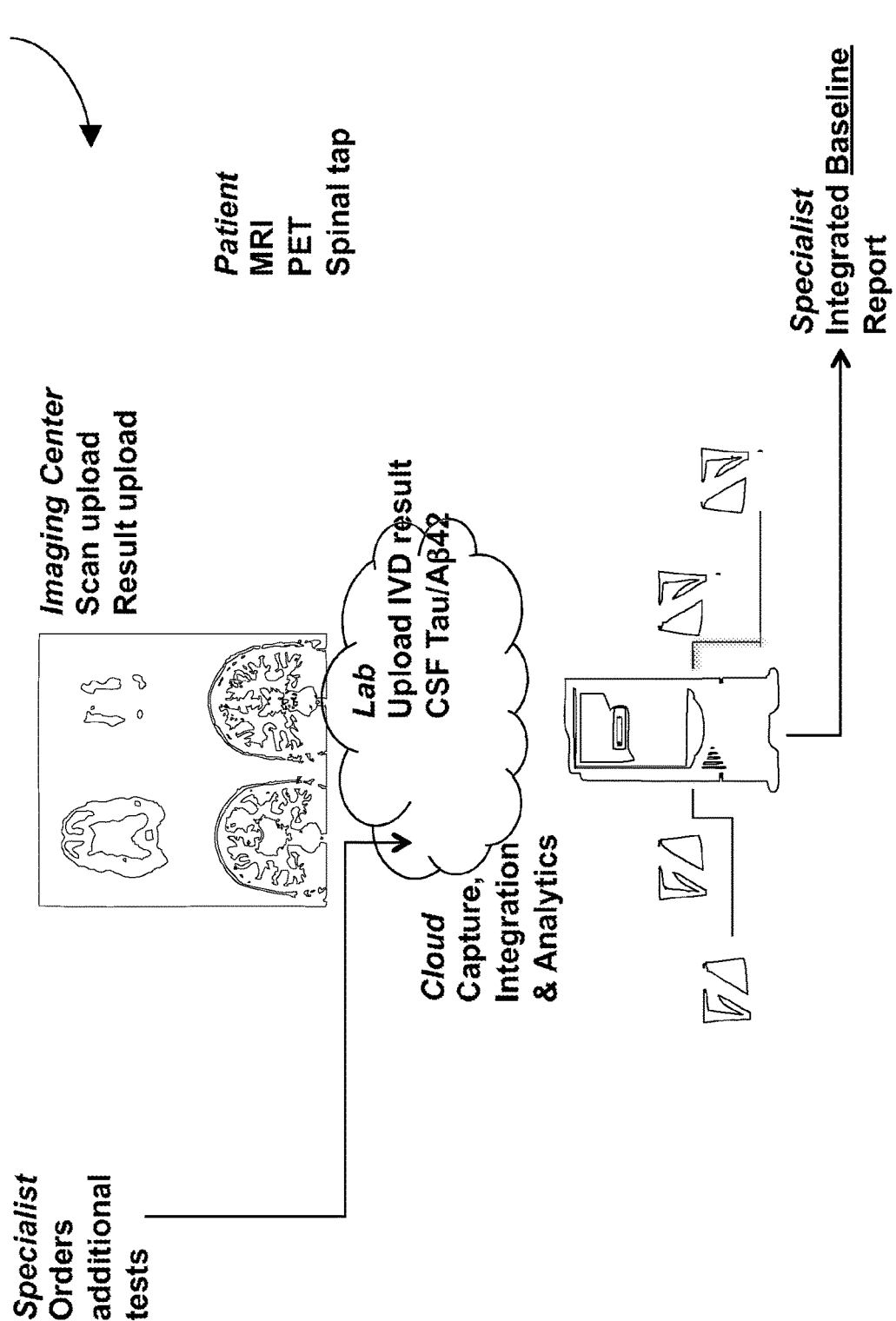

FIG. 11 is an example data flow of another example method 1100 of generating a report for presentation, arranged in accordance with at least some embodiments described herein. In some embodiments, the method 1100 may begin with a specialist having received a report indicating that a screening diagnostic evaluation be performed based on previously-collected data from a primary care physician. In some embodiments, the report received by the specialist may be analogous to the report received by the specialist in the method 1000.

In particular, the method 1100 is configured to generate an integrated "baseline" diagnostics report. The baseline diagnostics report may be a report that includes baseline data for a patient. The baseline data may be data that is gathered from a patient and used to compare to future data of the patient to determine the health of the patient. The baseline data determines baseline health characteristics of a patient.

The specialist may order additional tests for the patient, such as an MRI and/or a spinal tap and cerebrospinal fluid (CSF) assay for tau protein or amyloid beta peptide, which may be diagnostic markers of neurodegeneration and amyloid accumulation, respectively. The data from the additional tests may be uploaded into the cloud of the social network and combined with or not combined with the previous data collected for the patient. Data analytics may be performed on the combined data, such as automated quantitative MRI analysis, or a centralized quality-controlled expert read of a scan. The combined data and/or results from the analysis may be curated in a concise, summarized report as described earlier. In some embodiments, the report may be the integrated baseline diagnostic report. The integrated baseline diagnostic report may be shared with another physician in the social network, for instance, the patient's primary care physician. In some embodiments, the specialist may further consult on the integrated report's data with a data interpretation expert such as in a call center, via voice, video, or other messaging within the social network.

Figure 12:
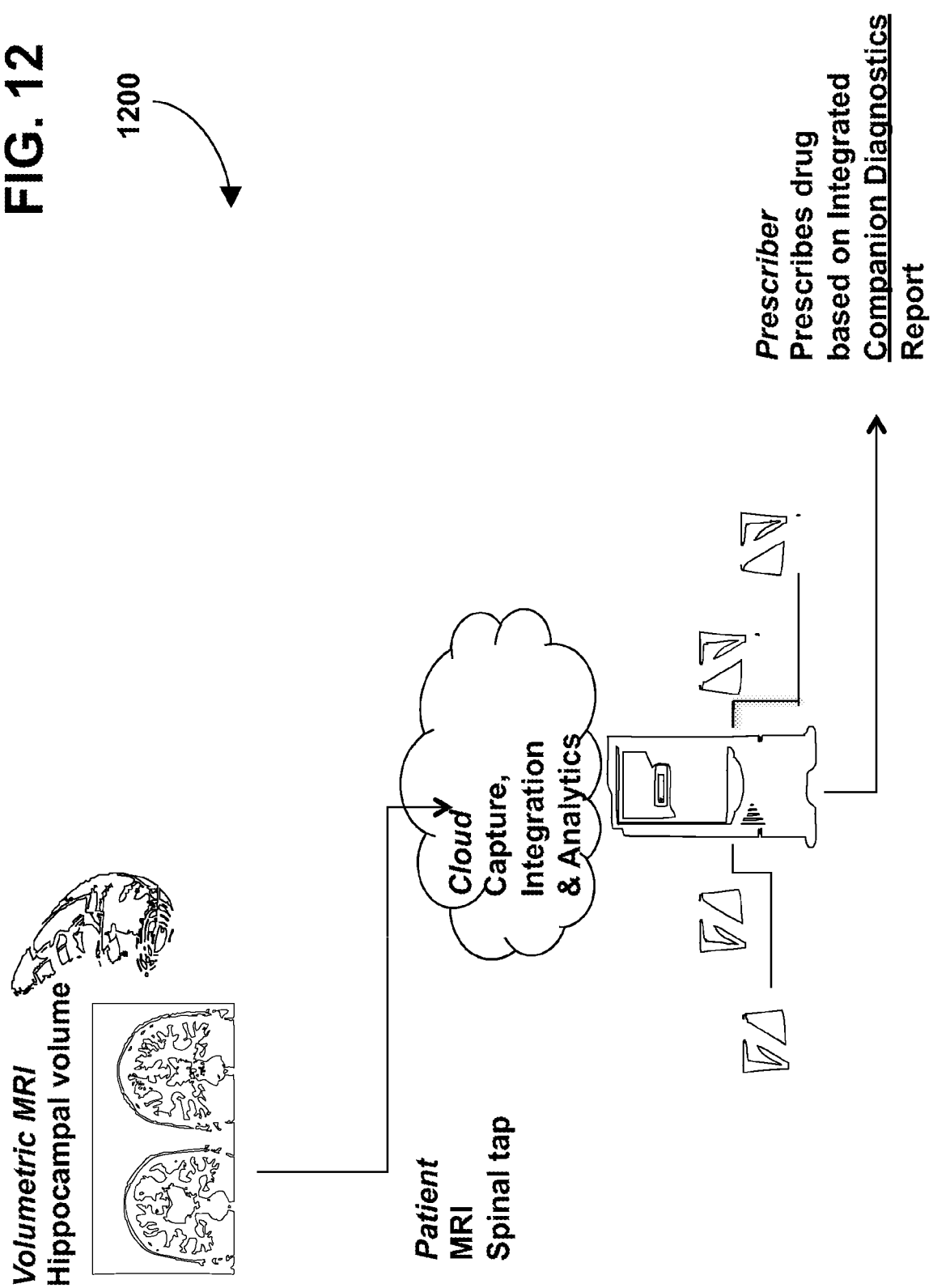

FIG. 12 is an example data flow of another example method 1200 of generating a report, arranged in accordance with at least some embodiments described herein. For example, in the method 1200, an integrated "companion diagnostics" report may be generated from a subset of a diagnostic evaluation of a patient. The diagnostic evaluation, for example, may include a quantitation of hippocampal volume based on Mill. The diagnostic evaluation may also include other biomarkers, such as a cerebrospinal fluid (CSF) assay. The results from the diagnostic evaluation may be captured and inserted into a cloud of a social network. The diagnostic evaluation, once in the cloud, may be analyzed. The analytics, such a stratification based on machine learning or statistical algorithms described earlier, may applied to the diagnostic information from the patient and summarized into actionable personalized treatment information in the form of an integrated companion diagnostics report for a prescriber of a drug. The drug may include a disease-modifying drug for treatment of early AD, for example, in the prodromal disease stage. The integrated companion diagnostics report may present the values of the individual components of the diagnostics, plus a calculated combination score, together with label information of an approved personalized drug intended to be used with the combination biomarker as "companion diagnostics." The drug may be directly ordered from a device such as a tablet or wearable computer that is presenting the integrated companion diagnostics report. The integrated companion diagnostics report may further be shared with other physicians in the social network, such as a specialist.

Figure 13:
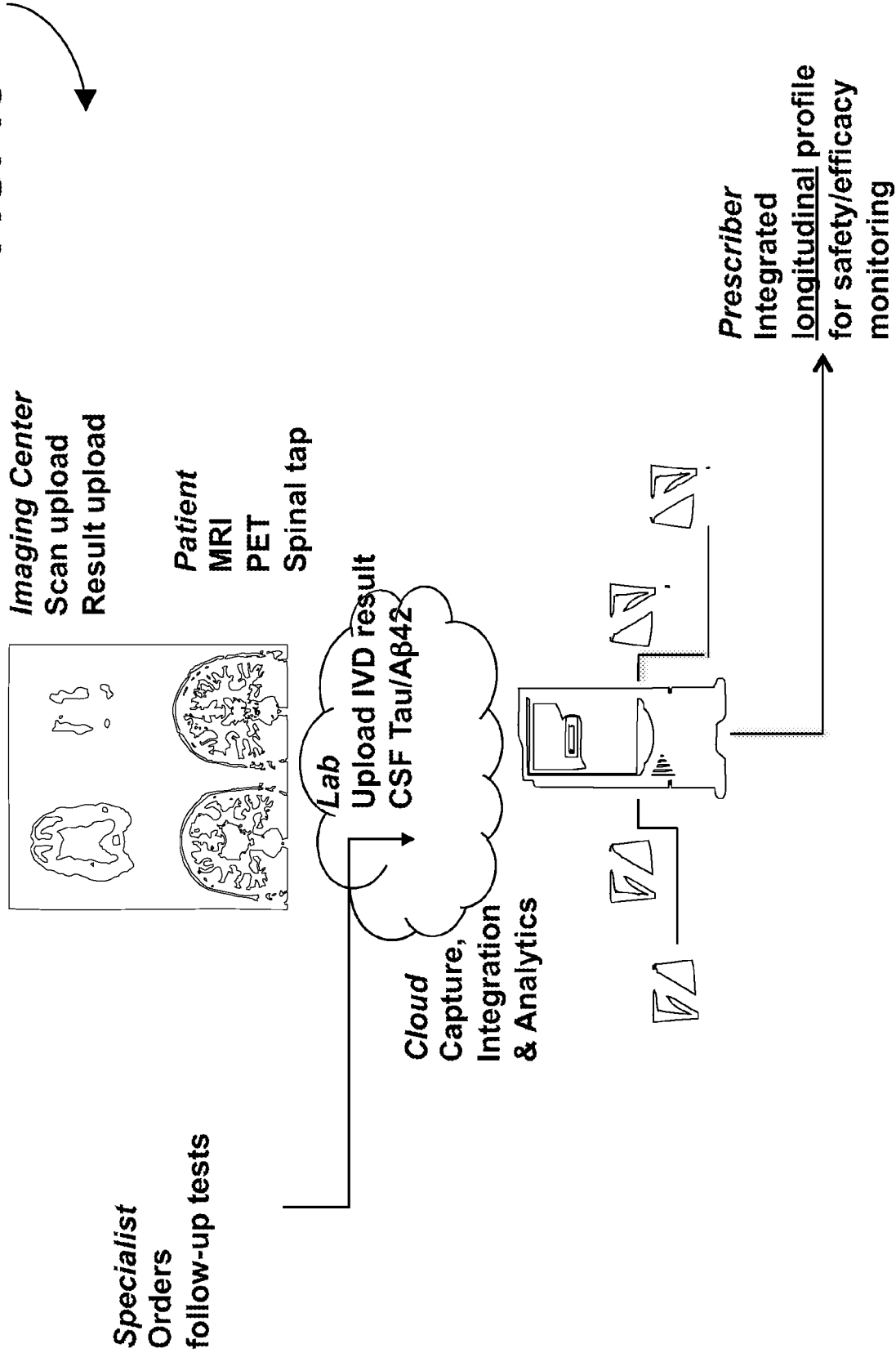

FIG. 13 is an example data flow of another example method 1300 of generating a report for presentation, arranged in accordance with at least some embodiments described herein. In some embodiments, the method 1300 may begin with a specialist having received a report indicating a need for integrated companion diagnostics that include actionable personalized treatment information for a patient. In some embodiments, the report received by the specialist may be similar to the report received by the specialist in the method 1200.

In particular, the method 1300 may be configured to generate an integrated longitudinal report for safety and efficacy monitoring. The report may be presented to a prescriber of a disease-modifying AD drug therapy or other AD therapy. Longitudinal monitoring over a period may include following a prescribed treatment for a patient to determine the benefit of the treatment to the patient and to determine whether the treatment is having any adverse effects on the patient, such as microhemorrhages or vasogenic edema (called ARIA-H or ARIA-E).

The longitudinal monitoring may include a specialist performing and/or ordering additional tests of the patient over the period. The tests may include CSF assays or PET scans for efficacy monitoring, such as measuring the level of amyloid beta in the CSF or amyloid load in the brain. Data analytics may be performed on the data, such as automated quantitative image analysis or a centralized quality-controlled expert read of a scan such as safety reads of MRIs, for presence of ARIA-H or ARIA-E. Based on the data analytics, alerts may then be triggered upon detection of potential safety concerns of the drug treatment. The alerts may trigger messaging within the social network to indicate to the specialist and other participants in the social network of the alert being triggered.

The longitudinal profile from the patient may be also curated in a concise, summarized form, as described earlier, into the integrated longitudinal efficacy/safety profile report for therapy monitoring. In some embodiments, the integrated longitudinal efficacy/safety profile report may be shared among participants within the social network, such as a specialist, a personal care provider of the patient, and/or the subject paying the medical bills of the patient, such as an insurance company. In some embodiments, the subject paying the medical bills of the patient may make payment on aspects of the treatment of the patient based on the success of the treatment being within an adequate risk/benefit ratio. The subject paying the medical bills of the patient prescriber may further consult on the integrated efficacy/safety profile data with another physician expert, for example, in a call center, via voice, video, or other messaging within the social network.

In some embodiments, the physician that prescribes the treatment for the patient may switch the treatment based on how the patient is responding to the treatment. In some embodiments, the subject paying the medical bills of the patient may mandate a change in treatment based on review of data.

The data analyzed for generating the integrated longitudinal efficacy/safety profile report may include other information about the patient. For example, the data analyzed may include the patient's individual characteristics, including next-generation genome sequencing information. Other patient characteristics collected from continuous wireless sensing devices may be incorporated to capture novel biomarkers, such as activity in multiple sclerosis (using mobile accelerometers) or micro-invasive, mobile blood sampling/ analysis in cancer therapy. In some embodiments, therapy monitoring may include therapy monitoring of a personalized drug therapy, such as antibody therapy, which may be applied in multiple sclerosis and other diseases such as cancer.

In some embodiments, the data from the patient may be anonymized and aggregated with anonymized data from other patients. The anonymized aggregated data may further be utilized by pharmaceutical companies for generating peri- or post-approval data and demonstrating real-world evidence of a favorable risk/benefit ratio, for instance, for reimbursement purposes.

Figure 14:
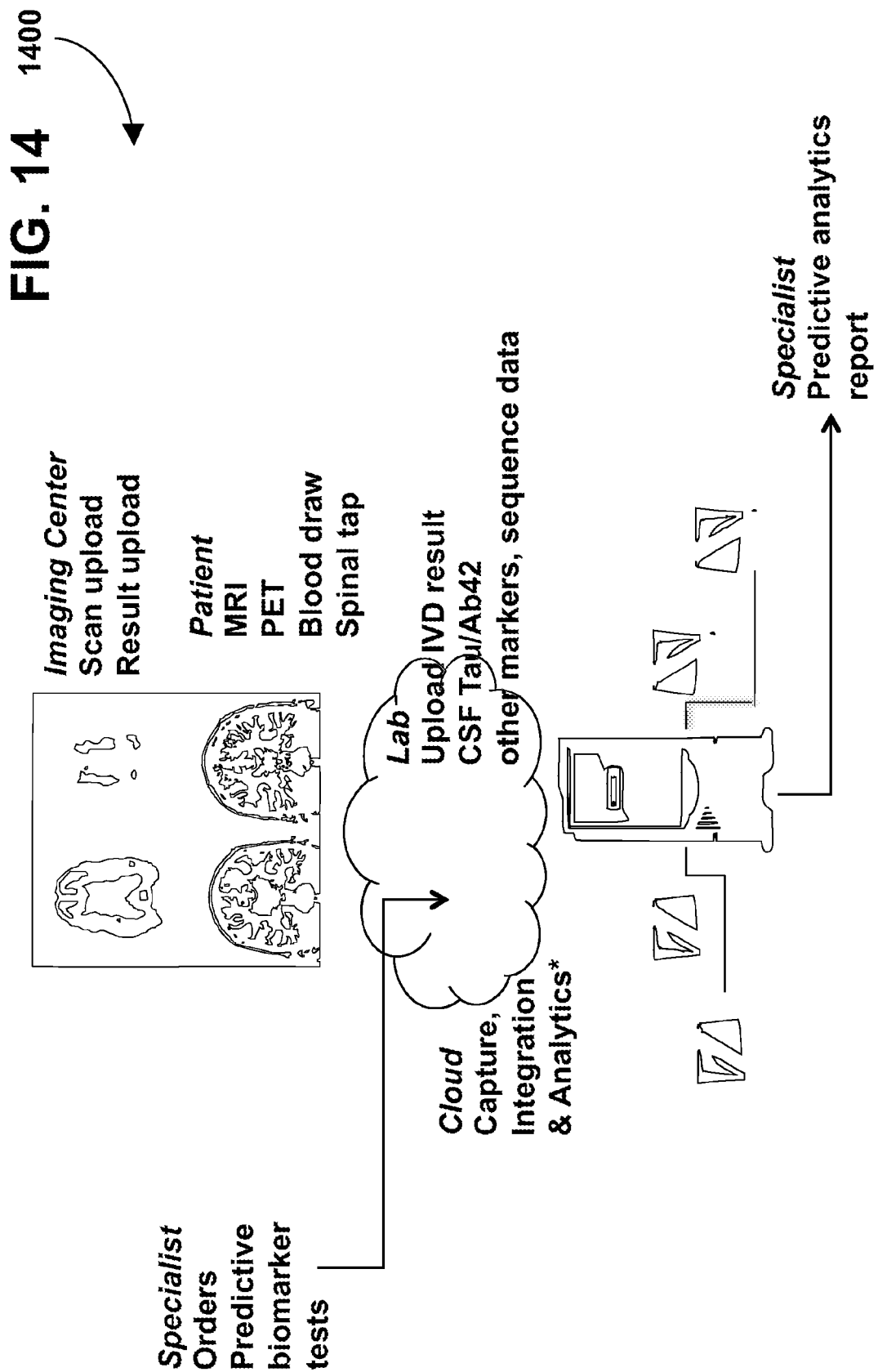

FIG. 14 is an example data flow of another method 1400 of generating a report for presentation, arranged in accordance with at least some embodiments described herein. The method 1400 may be configured to generate a predictive analytics report based on analytics of individual biomarkers, or integration of a multitude of biomarkers of a patient. The predictive analytics report may be generated for a physician, a subject paying the medical bills of the patient, or the patient, prior to the patient receiving a disease-modifying AD drug therapy or other AD therapy. The predictive report may predict individual response to a particular prevention strategy, such as prescribing a biologics drug in the pre-symptomatic, earliest phase of AD. The predictive report may further identify at-risk individuals such as seniors, for instance, to their family members. The predictive report may further stratify patients into a particular stage of the AD disease continuum, such as the pre-symptomatic phase, or earlier, and guide treatments that may be approved for these phases of disease.

To generate predictive analytics report, the method 1400 may include a first physician, such as a specialist, ordering a set of predictive biomarker tests for the patient. The predictive biomarker tests may include an MRI scan, a PET scan, a structural MRI analysis, a DTI MRI tractography, a brain connectivity map analysis, a voxel-based amyloid PET analysis, or other advanced brain imaging test. The physician may further order lab-based test such as IVDs or whole genome sequencing, among others. In some embodiments, the whole genome sequencing may be performed on semiconductor-based nanopore sequencing equipment. The data collected from the lab-based tests and the predictive biomarker tests may be captured and combined together in a cloud in the social network, for example, the social network 100 of FIG. 1.

Automated data analytics may be performed on the combined data, as described earlier. The automated data analytics may be performed in an analytic data center in a building or office of the physician, in a physical analytic data center, in a physical supercomputer facility, in a cloud-based on-demand compute resource such as Amazon EC2, or in a dedicated analytic data center in the cloud. In these and other embodiments, the analytic data center may be communicatively coupled to the social network to receive the combined data from the social network. The analytic data center may further utilize quantum computers, nodes with integrated quantum chips, or nodes optimized for in-memory analytics such as tera- or petabyte-order memory.

In some embodiments, the advanced analytics may include real time, automated quantitative analysis of hippocampal volumes or other brain structures, fiber tract network analysis based on DTI MRI, or brain connectivity map analysis based on ultra-high resolution resting state fMRI, among other analytics. The advanced analytics may further include NGS genome analysis, analysis of mass spectrometry data, and/or analysis of a combination of biomarkers.

Once the analytics are performed, the physician, such as a specialist, may use a tablet or wearable computer device with a natural user interface (NUI) to access the advanced analytics capabilities residing in the analytic data center or compute resource that is connected to the social network. In some embodiments, the physician may navigate the NUI to identify a set of useful additional predictive biomarker tests to be performed, based on information already available for the patient and data residing in the aggregated data repository. In some embodiments, the NUI may invoke advanced analytics to be run against the data repository, for example, to identify such useful additional markers. After identifying the additional markers, the NUI may then present the result back to the physician or other participant in the social network. In some embodiments, the advanced analytics report may include data presented in a quantitative format such as probability, likelihood, and/or score, alongside contextual information from the literature explaining the predictive analytics result. In these and other embodiments, the physician may directly order these predictive tests from the social network so they can be performed on data from the patient and summarized in the predictive analytics report.

FIGS. 10-14 illustrate particular methods for generating reports related to Alzheimer's disease. In general, the methods and systems described herein may be applicable to any personalized health care application and therapy area, for example, other neurodegenerative diseases, multiple sclerosis, and cancer. The methods and systems described may also be implemented for application in the diagnosis of post-traumatic stress disorder (PTSD) or traumatic brain injury (TBI). PTSD and TBI may share common elements in diagnostic approach and have been hypothesized as being a contributor to the development of subsequent AD dementia. Other embodiments may incorporate other imaging modalities, such as FDG-PET, molecular imaging such as nanoparticle based MRI, DTI MRI, ASL MRI, and so on. Other non-imaging biomarkers, for example, via continuous wireless monitoring and/or "self tracking" consumer devices, such as by gait sensors, eye tracking, wireless sleep monitors such as accelerometers and/or EEG, etc., may be implemented using Continua Alliance/ISO/IEEE 11073 Personal Health Data (PHD) standards.

Figure 15:
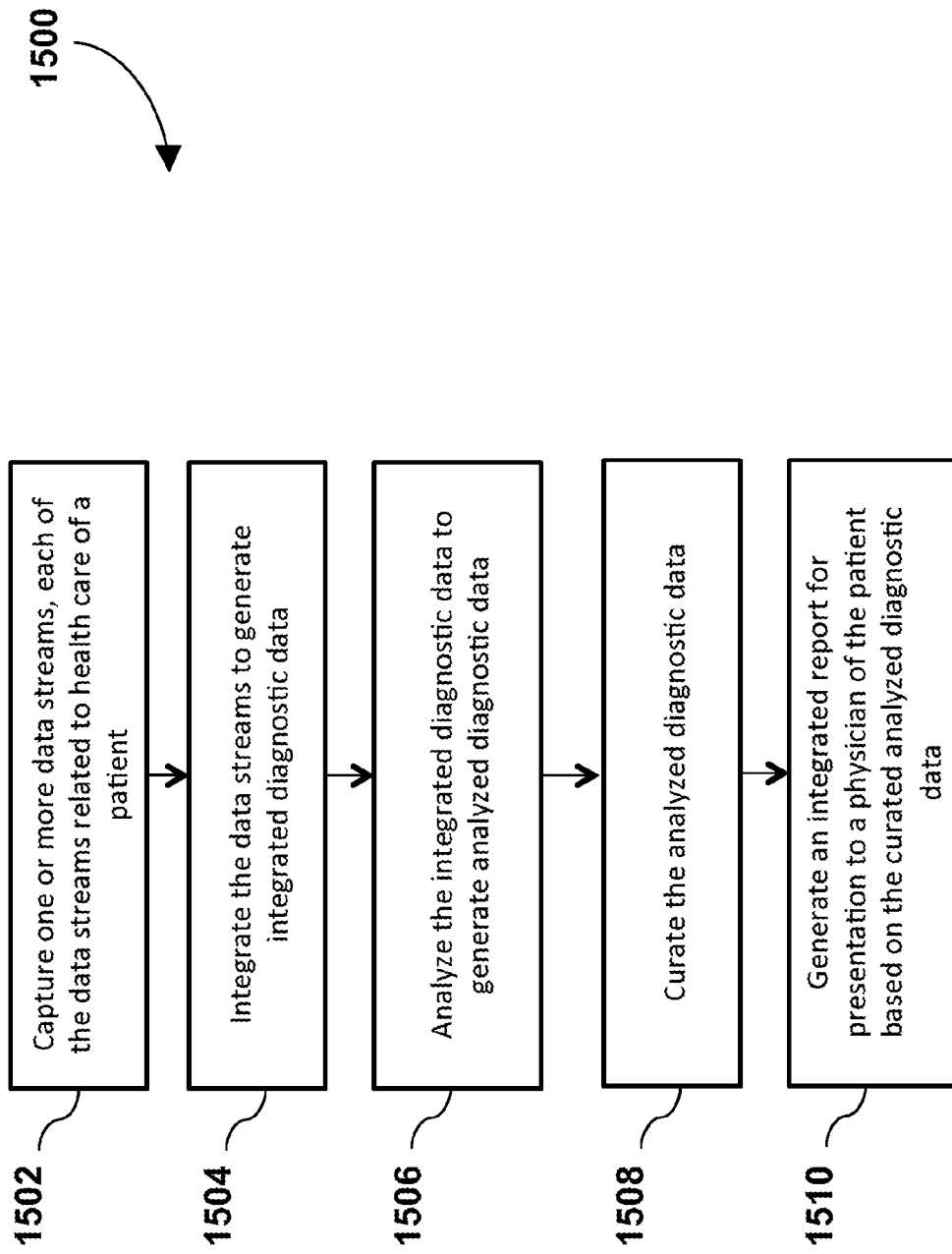
FIG. 15 is a flowchart of an example method of delivering information-enabled personalized health care in a clinical, non-research setting.

FIG. 15 is a flow chart of an example method 1500 of delivering information-enabled personalized healthcare in a clinical, non-research setting, arranged in accordance with at least some embodiments described herein. The method 1500 may be implemented, in some embodiments, by a system, such as the system 800 of FIG. 8. Although illustrated as discrete blocks, various blocks may be divided into additional blocks, combined into fewer blocks, or eliminated, depending on the desired implementation.

The method 1500 may begin at block 1502, where one or more data streams may be captured. Each of the data streams may be related to health care of a patient. In some embodiments, one of the data streams may be captured from an application being run on a mobile device related to screening for early Alzheimer's disease. In some embodiments, one of the data streams may be captured from a mobile cognitive testing application being run on a mobile device with respect to the patient. In these and other embodiments, when the mobile cognitive testing application indicates a positive diagnostic, another of the data streams is captured from a genetic test ordered for the patient from within the mobile cognitive testing application. In some embodiments, the data streams may come from other patient test results. In some embodiments, the test results may be test results from the same type of tests where the tests are performed separately over-time or longitudinally. In some embodiments, the test results may come from a patient, a lab, a specialist, or a primary care physician. In some embodiments, the data stream may include images or written text, among other types of data.

In block 1504, the data streams may be integrated to generate integrated diagnostic data. In some embodiments, the data streams may be integrated in a cloud environment. In these and other embodiments, the data streams may be associated based on a patient from which the data streams originated. In some embodiments, the data streams may be accessed through a social network.

In block 1506, the integrated diagnostic data may be analyzed to generate analyzed diagnostic data. The analysis of the integrated diagnostic data may be performed, in some embodiments, by comparing the integrated diagnostic data with integrated diagnostic data of one or more other patients that are distinct from the patient or other data.

In block 1508, the analyzed diagnostic data may be curated. Curating the analyzed diagnostic data may include presenting one or several biomarkers alongside contextual information such as medical guidelines and/or relevant excerpts from the medical literature or links to the original references. Biomarkers may further be presented alongside normative and/or age-related ranges, plots of the patient's individual value in relation to the normative and/or age related ranges, and medical images of the patient or representative illustrative other cases.

In block 1510, an integrated report for presentation to a physician of the patient may be generated based on the curated analyzed diagnostic data. In some embodiments, the report may provide information regarding drug therapy for the patient based on the analyzed diagnostic data.

In some embodiments, the method 1500 may be performed in a cloud-based digital health platform for personalized health care with respect to Alzheimer's disease. In some embodiments, the health care diagnostics of the patient may relate to a baseline diagnosis of Alzheimer's disease such that the integrated report is a baseline integrated report. In some embodiments, the health care diagnostics of the patient may relate to a longitudinal monitoring of Alzheimer's disease within the patient such that the integrated report is an integrated longitudinal safety/efficacy monitoring report.

In some embodiments, the health care diagnostics of the patient may relate to therapy monitoring of disease-modifying multiple sclerosis therapeutics such that the integrated report is an integrated longitudinal safety/efficacy monitoring report.

In some embodiments, the health care diagnostics of the patient may relate to biomarkers of the patient, including gene sequencing data and the analyzing of the integrated diagnostic data includes predictive analytics such that the report is a predictive analytics report. In these and other embodiments, the predictive analytics may predict Alzheimer's disease at a pre-symptomatic stage. Alternately or additionally, the predictive analytics may predict a response of a patient to a particular therapy.

Tables 1-3 show a group of single-nucleotide polymorphisms (SNPs) that were generated by a quantitative trait locus genome wide association study (QTL GWAS), including four novel Alzheimer's Disease (AD) specific disease targets with protective and risk properties, that can be used for diagnostic and/or therapeutic use in personalized medicine.

Table 1 is an example of a group of SNPs that were identified by a QTL GWAS, using PLINK, wherein the quantitative trait is a voxel-based Amyloid PET quantitation reflecting Alzheimer's disease activity. Genotyping was performed using the Illumina Omni2.5 microarray. Table 1 shows the result of an association study and respective SNP ranking (ID), chromosome (Chr), SNP (accession number, also called rsid identifying the variant), p-value, minor allele carrier counts (total discovery sample n=334), as well as the variant alleles/bases (A1 denotes the minor allele and A2 denotes the major allele). The minor allele can be considered the SNP for the purposes of determining the SNP showing a reduced chance or increased chance of disease. The major allele is the common allele that provides an indication opposite of what is provided by the minor allele.

Four novel Alzheimer's specific disease targets (see Table 3) were identified and highlighted (Table 1) in the RTTN, ALCAM, DMXL2, DYNLL1 genes, where the minor allele provides the indication of being protective so as to have a reduced chance of Alzheimer's disease, or being at risk or having an elevated chance of Alzheimer's disease: rs4891826 (RTTN), rs2030515 (ALCAM), rs7164265 (DMXL2), rs993900 (DYNLL1). It was found that the following two SNPS may show a reduced likelihood of onset of Alzheimer's disease: rs4891826 (RTTN), rs2030515 (ALCAM) (both with protective property, indicated by * for the respective minor alleles as shown in Table 1), where the presence of these two SNPs indicate no Alzheimer's disease or a decreased risk of development thereof. The presence of the other two SNPs indicate Alzheimer's disease risk for the respective minor alleles: rs7164265 (DMXL2), rs993900 (DYNLL1).

Table 2 shows the same association study, but now corrected for APOE4 carrier status. In the latter, the ranking has changed and the RTTN variant minor allele rs4891826 is revealed as the top SNP after correcting for APOE4 carrier status. In Table 1 and 2, the base corresponding to risk or protective (*) property as revealed by the QTL GWAS can be found in column A1 for the minor allele. One skilled in the art will appreciate that even though A1 is the minor allele in this QTL GWAS example, the designation of minor allele (MA) is depending on the population minor allele frequency (MAF) used for the association study, and actual base letter substitution may need to be translated depending on genotyping method and coding/reporting standard used during analysis. For example, for rs993900 the base revealed as risk associated is A, however if reported in reverse strand orientation it is T.

TABLE 1

QTL GWAS Top 50 SNPs

| ID | Chr | SNP | P | COUNTS (carrier) | A1 | A2 |
|---|---|---|---|---|---|---|
| 1 | 19 | rs769449 | 4.13E−13 | 96 | A | G |
| 2 | 19 | rs4420638 | 1.10E−10 | 139 | G | A |
| 3 | 19 | rs56131196 | 1.44E−10 | 138 | A | G |
| 4 | 19 | rs2075650 | 3.11E−08 | 112 | G | A |
| 5 | 19 | rs71352238 | 8.41E−08 | 113 | C | T |
| 6 | 8 | rs10956245 | 1.30E−07 | 46 | T | C |
| 7 | 19 | rs157582 | 2.52E−07 | 159 | A | G |
| 8 | 19 | rs283815 | 3.04E−07 | 157 | G | A |
| 9 | 0 | kgp22786869 | 3.35E−07 | 144 | T | G |
| 10 | 19 | rs34095326 | 6.89E−07 | 90 | A | G |
| 11 | 19 | rs75627662 | 2.23E−06 | 118 | T | C |
| 12 | 1 | rs114798373 | 2.40E−06 | 16 | A | G |
| 13 | 4 | rs4689137 | 3.69E−06 | 169 | G | C |
| 14 | 4 | rs4698481 | 5.21E−06 | 98 | A | G |
| 15 | 7 | rs963281 | 6.02E−06 | 135 | C | T |
| 16 | 7 | rs2463471 | 6.70E−06 | 136 | C | T |
| 17 | 7 | rs10234008 | 6.77E−06 | 170 | T | C |
| 18 | 7 | rs17680408 | 6.86E−06 | 172 | A | G |
| 19 | 4 | rs10029820 | 6.87E−06 | 124 | G | A |
| 20 | 2 | rs2357394 | 7.38E−06 | 144 | A | G |
| 21 | 7 | rs993900 | 7.42E−06 | 137 | A | G |
| 22 | 7 | rs2033296 | 7.42E−06 | 137 | T | C |
| 23 | 15 | rs7164265 | 8.90E−06 | 196 | C | T |
| 24 | 7 | rs13222318 | 9.13E−06 | 218 | C | T |
| 25 | 6 | rs114979482 | 9.82E−06 | 29 | A | G |
| 26 | 18 | rs4891826 * | 1.01E−05 | 167 | G | T |
| 27 | 7 | rs62444137 | 1.07E−05 | 173 | A | G |
| 28 | 16 | rs6499632 | 1.14E−05 | 247 | C | T |
| 29 | 8 | rs62532372 | 1.17E−05 | 27 | A | G |
| 30 | 7 | rs1001029 | 1.38E−05 | 213 | A | G |
| 31 | 7 | rs1001026 | 1.38E−05 | 213 | A | G |
| 32 | 15 | rs1551466 | 1.43E−05 | 216 | C | G |
| 33 | 19 | rs368475 | 1.45E−05 | 44 | T | G |
| 34 | 1 | rs5031052 | 1.50E−05 | 8 | T | C |
| 35 | 7 | rs917321 | 1.50E−05 | 201 | T | C |
| 36 | 3 | rs2030515 * | 1.64E−05 | 215 | G | A |
| 37 | 7 | rs2463472 | 1.68E−05 | 180 | C | T |
| 38 | 7 | rs2049670 | 1.68E−05 | 180 | G | A |
| 39 | 15 | rs75300677 | 1.71E−05 | 17 | C | A |
| 40 | 9 | rs4842247 | 1.72E−05 | 197 | A | G |
| 41 | 15 | rs12916234 | 1.73E−05 | 212 | A | C |
| 42 | 4 | rs10007765 | 1.84E−05 | 117 | C | G |
| 43 | 7 | rs17165129 | 1.85E−05 | 17 | A | C |
| 44 | 14 | rs213563 | 1.90E−05 | 192 | A | G |
| 45 | 15 | rs116974206 | 2.14E−05 | 11 | G | T |
| 46 | 1 | rs11249026 | 2.23E−05 | 183 | C | T |
| 47 | 7 | rs17159900 | 2.26E−05 | 175 | G | T |
| 48 | 7 | rs67366748 | 2.36E−05 | 178 | G | A |
| 49 | 2 | rs4663541 | 2.37E−05 | 209 | A | G |
| 50 | 6 | rs1891517 | 2.39E−05 | 236 | T | C |

TABLE 2

QTL GWAS Top 50 SNPs (Apoe4 corrected)

| ID | Chr | SNP | P | COUNTS (carrier) | A1 | A2 |
|---|---|---|---|---|---|---|
| 1 | 18 | rs4891826 * | 9.23E−07 | 167 | G | T |
| 2 | 14 | rs55867246 | 1.90E−06 | 47 | A | G |
| 3 | 1 | rs114798373 | 2.59E−06 | 16 | A | G |
| 4 | 10 | rs1930458 | 2.90E−06 | 83 | A | G |
| 5 | 9 | rs4842247 | 2.91E−06 | 197 | A | G |
| 6 | 10 | rs1999505 | 4.17E−06 | 65 | C | A |
| 7 | 3 | rs1427780 | 4.47E−06 | 227 | A | G |
| 8 | 3 | rs13071744 | 4.77E−06 | 228 | G | T |
| 9 | 7 | rs2463471 | 6.11E−06 | 136 | C | T |
| 10 | 7 | rs993900 | 6.53E−06 | 137 | A | G |
| 11 | 7 | rs2033296 | 6.53E−06 | 137 | T | C |
| 12 | 7 | rs963281 | 7.70E−06 | 135 | C | T |
| 13 | 6 | rs114979482 | 8.07E−06 | 29 | A | G |
| 14 | 12 | rs143970600 | 8.08E−06 | 7 | C | A |
| 15 | 1 | rs6576798 | 9.86E−06 | 259 | C | T |
| 16 | 7 | rs13222318 | 1.10E−05 | 218 | C | T |
| 17 | 10 | rs11006004 | 1.28E−05 | 87 | G | A |
| 18 | 15 | rs4357923 | 1.29E−05 | 237 | A | G |
| 19 | 4 | rs4689137 | 1.37E−05 | 169 | G | C |
| 20 | 15 | rs7164265 | 1.40E−05 | 196 | C | T |
| 21 | 14 | rs12589674 | 1.44E−05 | 67 | C | A |
| 22 | 5 | rs2174147 | 1.45E−05 | 183 | A | C |
| 23 | 14 | rs8009420 | 1.59E−05 | 78 | A | C |
| 24 | 19 | rs17815373 | 1.61E−05 | 125 | A | G |
| 25 | 1 | rs11161719 | 1.64E−05 | 249 | C | T |
| 26 | 5 | rs10515601 | 1.68E−05 | 78 | T | G |
| 27 | 15 | rs1874848 | 1.81E−05 | 85 | A | G |
| 28 | 5 | rs78323632 | 1.87E−05 | 12 | C | T |
| 29 | 15 | rs111851441 | 2.03E−05 | 85 | T | C |
| 30 | 7 | rs1001029 | 2.05E−05 | 213 | A | G |
| 31 | 7 | rs1001026 | 2.05E−05 | 213 | A | G |
| 32 | 15 | rs9920618 | 2.41E−05 | 233 | C | T |
| 33 | 5 | rs11740072 | 2.45E−05 | 237 | C | T |
| 34 | 15 | rs1551466 | 2.49E−05 | 216 | C | G |
| 35 | 15 | rs78252085 | 2.66E−05 | 32 | C | T |
| 36 | 1 | rs4845054 | 2.80E−05 | 31 | T | C |
| 37 | 12 | rs1086013 | 2.81E−05 | 46 | G | A |
| 38 | 12 | rs4508236 | 2.81E−05 | 46 | T | C |
| 39 | 6 | rs9458512 | 2.99E−05 | 108 | A | G |
| 40 | 11 | rs17147461 | 3.20E−05 | 48 | A | G |
| 41 | 15 | rs78341108 | 3.21E−05 | 23 | T | G |
| 42 | 5 | rs6866169 | 3.28E−05 | 188 | C | T |
| 43 | 14 | rs72681708 | 3.29E−05 | 45 | C | A |
| 44 | 1 | rs4912453 | 3.36E−05 | 257 | T | C |
| 45 | 1 | rs12120406 | 3.36E−05 | 257 | G | A |
| 46 | 16 | rs8056050 | 3.44E−05 | 132 | C | T |
| 47 | 15 | rs11638857 | 3.51E−05 | 57 | T | G |
| 48 | 4 | rs62337205 | 3.53E−05 | 26 | G | A |
| 49 | 4 | rs62337211 | 3.53E−05 | 26 | A | C |
| 50 | 2 | rs13429381 | 3.62E−05 | 6 | G | T |

TABLE 3

| SNP | Novel target property | Gene/protein |
|---|---|---|
| rs4891826 | * protective | RTTN |
| rs2030515 | * protective | ALCAM/CD166 |
| rs7164265 | risk | DMXL2 |
| rs993900 | risk | DYNLL1 |

Figure 16:
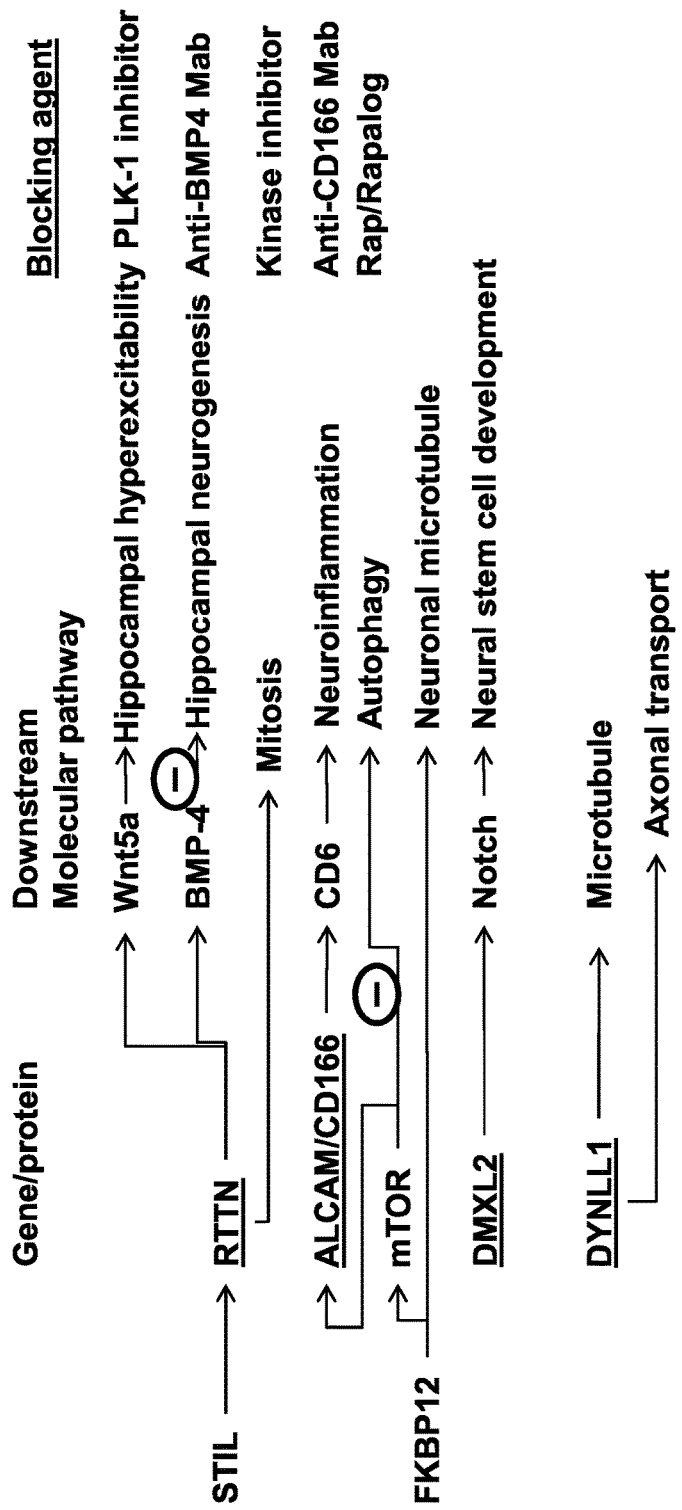
FIG. 16 is a diagram illustrating the scientific rationale of four novel targets for diagnostic (Dx) and/or therapeutic (Rx) use in AD personalized medicine.

FIG. 16 is a diagram illustrating the scientific rationale of the four novel targets for diagnostic (Dx) and/or therapeutic (Rx) use in AD personalized medicine. The respective genes/proteins and downstream molecular pathways are resulting in several therapeutic avenues, when used in connection with said SNPs (e.g., minor alleles), rs4891826 (G), rs2030515 (G), rs7164265 (C), and/or rs993900 (A). Therapeutic intervention targeting hippocampal hyperexcitability, hippocampal neurogenesis, neuroinflammation, neural stem cell development, and axonal transport individually or in combination may be of particular interest.

Now, the combination of at least one of the said four novel Alzheimer's disease associated variant alleles (e.g., related SNPs having minor allele), rs4891826 (G), rs2030515 (G), rs7164265 (C), and/or rs993900 (A), for diagnostic and/or therapeutic use in personalized medicine may be embodied in a computer-implemented method of delivering information-enabled personalized health care with respect to early Alzheimer's disease in a clinical, non-research setting, comprising a social network, and may include capturing one or more data streams where each of the data streams relates to health care of an individual patient, wherein the method may further include integrating the data streams to generate integrated diagnostic data and analyzing the integrated diagnostic data to generate analyzed diagnostic data, and wherein the method may further include curating the analyzed diagnostic data and generating an integrated report for presentation to a physician of the patient based on the curated analyzed diagnostic data, as described in more detail above.

In one embodiment, at least one of the one or more data streams is captured having genetic data obtained from genetically testing for one or more certain genetic variations that include one or more single-nucleotide polymorphisms (SNPs) minor alleles selected from a group of SNPs. In one aspect, the selected one or more SNPs include at least one of the following SNPs minor alleles in genes RTTN, ALCAM, DMXL2, or DYNLL1 of the individual patient: rs4891826 (G), rs2030515 (G), rs7164265 (C), or rs993900 (A).

At least one of the data streams in said computer-implemented method may include the diagnostic testing for at least one of the four novel SNP biomarkers, rs4891826 (G), rs2030515 (G), rs7164265 (C), and/or rs993900 (A), and may further include one or more of the minor allele (A1) of the following:

rs769449, rs4420638, rs56131196, rs2075650, rs71352238, rs10956245, rs157582, rs283815, rs34095326, rs75627662, rs114798373, rs4689137, rs4698481, rs963281, rs2463471, rs10234008, rs17680408, rs10029820, rs2357394, rs2033296, rs114979482, rs62444137, rs6499632, rs62532372 rs1001029, rs1001026, rs1551466, rs368475, rs5031052, rs917321, rs2463472, rs2049670, rs75300677, rs4842247, rs12916234, rs10007765, rs17165129, rs213563, and/or rs55867246, rs1930458, rs1999505, rs1427780 rs13071744, rs6576798, rs13222318, rs11006004, rs4357923, rs12589674, rs2174147, rs8009420, rs17815373, rs11161719, rs10515601, rs1874848, rs78323632, rs111851441, rs9920618, rs11740072, rs78252085 rs4845054, rs1086013, rs4508236, rs9458512, rs17147461, rs78341108, rs6866169, rs72681708, rs4912453, rs12120406, rs8056050.

In one embodiment, the said computer-implemented method may then be applied for providing a personalized therapy, wherein the personalized therapy is an antibody against the BMP-4 protein (anti-BMP-4 antibody) or functional fragment thereof when the individual patient does not test positive (i.e., is a non-carrier) for the protective rs4891826 (G) SNP.

In one embodiment, the said computer-implemented method may further include predictive analytics, whereas the predictive analytics is based on a social network analysis (SNA) of the gene/protein molecular network with respect to the included/selected SNPs and wherein the personalized therapy is a small molecule oncology kinase inhibitor selected based on the SNA.

In one embodiment, the said computer-implemented method may further be applied for providing a personalized therapy, wherein the personalized therapy is small molecule oncology kinase inhibitor when the individual patient does not test positive (i.e., is a non-carrier) for the protective rs4891826 (G) SNP.

In one embodiment, the said computer-implemented method may further be applied for providing a personalized therapy, wherein the personalized therapy is an antibody against the ALCAM/CD166 protein (anti-CD166 antibody) or functional fragment thereof when the individual patient does not test positive (i.e., is a non-carrier) for the protective rs2030515 (G) SNP.

In one embodiment, the said computer-implemented method may further be applied for providing a personalized therapy, wherein the personalized therapy is an mTOR inhibitor (e.g., rapamycin, or rapalog) when the individual patient does not test positive (i.e., is a non-carrier) for the protective rs2030515 (G) SNP.

In one embodiment, the said computer-implemented method may further be applied for providing a personalized therapy, wherein the personalized therapy is a combination therapy of an anti-BMP-4 antibody or functional fragment thereof and an mTOR inhibitor when the individual patient does not test positive (i.e, is a non-carrier) for both the protective rs4891826 (G) and rs2030515 (G) SNPs.

In one embodiment, the said computer-implemented method may further be applied for providing a personalized therapy, wherein the personalized therapy is gene editing or trans-epigenetic modulation using CRISPR, in the RTTN, ALCAM, DMXL2, or DYNLL1 genes based on the testing for said rs4891826 (G), rs2030515 (G), rs7164265 (C), or rs993900 (A) SNPs and may further include one or more of the minor allele (A1) of the following:

rs769449, rs4420638, rs56131196, rs2075650, rs71352238, rs10956245, rs157582, rs283815, rs34095326, rs75627662, rs114798373, rs4689137, rs4698481, rs963281, rs2463471, rs10234008, rs17680408, rs10029820, rs2357394, rs2033296, rs114979482, rs62444137, rs6499632, rs62532372 rs1001029, rs1001026, rs1551466, rs368475, rs5031052, rs917321, rs2463472, rs2049670, rs75300677, rs4842247, rs12916234, rs10007765, rs17165129, rs213563, and/or rs55867246, rs1930458, rs1999505, rs1427780 rs13071744, rs6576798, rs13222318, rs11006004, rs4357923, rs12589674, rs2174147, rs8009420, rs17815373, rs11161719, rs10515601, rs1874848, rs78323632, rs111851441, rs9920618, rs11740072, rs78252085 rs4845054, rs1086013, rs4508236, rs9458512, rs17147461, rs78341108, rs6866169, rs72681708, rs4912453, rs12120406, rs8056050;

Other nuclease systems, such as ZFN or TALEN may also be used for gene editing. Gene editing may be applied to human neural stem cells of the individual patient which may then be delivered into the individual patient's brain using a minimally invasive surgical procedure, for example image-guided (such as MRI-guided) delivery directly into targeted brain structures often affected by Alzheimer's disease, such as the hippocampus or precuneus. Image guided delivery of gene edited cells such as the individual patient's neural stem cells may be combined in the same session, with the image quantitation described above, such as hippocampus quantitation, voxel-based image quantitation, texture analysis of magnetic resonance imaging (MRI) scans, or brain connectome analysis based on diffusion tensor imaging (DTI) fiber tracking. The image quantitation may also be used for targeting delivery of the gene edited cells, such as by location of disease activity. The neural stem cells may also be delivered by injection into individual patient's spinal fluid space.

In one embodiment, the said gene editing may be performed by the lab 718 (FIG. 7), which is part of the social network for personalized medicine, and based on said testing for the at least one of said rs4891826 (G), rs2030515 (G), rs7164265 (C), or rs993900 (A) SNPs. The testing for said SNPs may be performed by the same lab that performs the gene editing or another lab connected to the social network for personalized medicine. It is foreseeable that gene editing may be run in an automated and multiplexed fashion on an integrated device and/or integrated into a next-generation genome sequencing device, and coupled with the social network for personalized medicine, as described earlier.

In one embodiment, the said computer-implemented method may further be applied for providing a personalized therapy, wherein the personalized therapy is an antisense oligonucleotide (ASO) or short-interfering RNA (siRNA) therapy targeting the ALCAM/CD166 gene, when the individual patient does not test positive (i.e, is a non-carrier) for the protective rs2030515 (G) SNP.

Now, said gene editing may further be targeting the ALCAM gene of an individual patient such that the modified, gene edited stem cells carry two copies of the protective rs2030515 variant (i.e., are homozygous) so that the individual patient may particularly benefit from effects of the protective rs2030515 variant.

In one embodiment, the analysis of at least one of said four novel Alzheimer's disease associated variant alleles, rs4891826 (G), rs2030515 (G), rs7164265 (C), or rs993900 (A), for diagnostic and/or therapeutic use in personalized medicine may further be embodied in a method for detection of one SNP or a combination of SNPs in a human subject, comprising:

a) obtaining a nucleic acid sample from said human subject;

b) genotyping the sample for a combination of Alzheimer's disease associated genes(s) RTTN, ALCAM/CD166, DMXL2, or DYNLL1, said one SNP or combination of SNP alleles being at least one of the following: rs4891826 (G), rs2030515 (G), rs7164265 (C), or rs993900 (A);

c) detecting in said nucleic acid sample the presence of at least one of: a G for rs4891826, a G for rs2030515, a C for rs7164265, an A for rs993900.

In one embodiment, the combination is rs4891826 (G) and rs2030515 (G), which indicates the human subject has a protective trait that inhibits onset or development of Alzheimer's disease.

In one embodiment, the combination is rs7164265 (C) and rs993900 (A), which indicates the human subject has a risk of onset or development of Alzheimer's disease.

In one embodiment, a method includes testing for a combination of SNPs, where any one of the SNPs or a combination of two SNPs being present provides an indication of a disease state, such as Alzheimer's disease. As such, a combination of at least two, or three or four SNPs may be tested for the presence in a genome of an individual patient. The presence of at least one SNP from the group of SNPs may then be used for the computer methods described herein related to personalized therapeutics.

In one embodiment, a method for detection of at least one single nucleotide polymorphisms (SNPs) in a human subject from assaying a combination of SNPs can include: a) obtaining a nucleic acid sample from said human subject; b) genotyping the sample for a combination of Alzheimer's disease associated genes(s) RTTN, ALCAM/CD166, DMXL2, and DYNLL1, said combination of SNP alleles being the following: rs4891826 (G), rs2030515 (G), rs7164265 (C), and rs993900 (A); and c) detecting in said nucleic acid sample the presence of at least one of: a G for rs4891826, a G for rs2030515, a C for rs7164265, an A for rs993900. In one aspect, the assaying can be any experiment, protocol, investigation, sequencing or any kind of genotyping, such as NGS, microarray, PCR, or the like.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The embodiments described herein may include the use of a special purpose or general purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may comprise tangible (non-transient) computer-readable storage media including RAM, ROM, EEPROM, CD-ROM or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module," "sub-system," or "component" may refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A method of delivering information-enabled personalized health care with respect to early Alzheimer's disease in a clinical, non-research setting, the method comprising:
provisioning, using one or more servers, a healthcare social network particular to providing personalized health care for an individual patient, the healthcare social network configured to:
accept the individual patient as a new patient in the healthcare social network,
add content data for the individual patient, the content data including one or more physical measurements from diagnostic testing performed on the individual patient using testing equipment of a testing system coupled with the healthcare social network,
specify recipients within the healthcare social network particular to the individual patient for delivery of the content data, and
provide a secure interface for multiple participants particular to the individual patient to exchange bidirectional secure correspondence within the healthcare social network regarding the personalized health care of the individual patient and transfer the content data there between based on permissions within the healthcare social network,
capturing one or more data streams with the healthcare social network, each of the data streams related to health care of the individual patient provided by one or more of the multiple participants, wherein one or more of the data streams include the content data that includes results from the diagnostic testing of the individual patient,
wherein one of the data streams is captured from a next-generation sequencing (NGS) device as the testing equipment of the testing system having the content data for certain genetic variations in the individual patient including at least one detected single-nucleotide polymorphisms (SNPs), and further including one or more of a voxel-based imaging quantitation, a cerebrospinal fluid (CSF) assay for tau protein or amyloid beta peptide of the individual patient derived from a spinal tap procedure, or a blood test for Alzheimer's disease, performed on the individual patient;
generating a diagnostic profile for the individual patient that is based on the content data of the at least one detected SNPs, using the one or more processors;
curating, using the one or more processors, the diagnostic profile by presenting the diagnostic profile with contextual medical information to obtain a curated diagnostic profile; and
generating, using the one or more processors, an integrated report for presentation to a physician of the individual patient using the curated diagnostic profile, the integrated report for providing a personalized therapy for the individual patient with respect to the curated diagnostic profile.

2. The method of claim 1, wherein at least one of the one or more data streams is captured having genetic data obtained from genetically testing for one or more certain genetic variations that include one or more single-nucleotide polymorphisms (SNPs) minor alleles selected from a group of SNPs, and
wherein the selected one or more SNPs include at least one of the following SNPs minor alleles in genes RTTN, ALCAM, DMXL2, or DYNLL1 of the individual patient: rs4891826 (G), rs2030515 (G), rs7164265 (C), or rs993900 (A).

3. The method of claim 1, wherein one of the data streams is captured from an application being run on a mobile or wearable device related to screening for early Alzheimer's disease.

4. The method of claim 2, wherein the SNPs selected from the group of SNPs further include one or more of minor alleles of one or more of the following:
rs769449, rs4420638, rs56131196, rs2075650, rs71352238, rs10956245, rs157582, rs283815, rs34095326, rs75627662, rs114798373, rs4689137, rs4698481, rs963281, rs2463471, rs10234008, rs17680408, rs10029820, rs2357394, rs2033296, rs114979482, rs62444137, rs6499632, rs62532372 rs1001029, rs1001026, rs1551466, rs368475, rs5031052, rs917321, rs2463472, rs2049670, rs75300677, rs4842247, rs12916234, rs10007765, rs17165129, rs213563, rs55867246, rs1930458, rs1999505, rs1427780 rs13071744, rs6576798, rs13222318, rs11006004, rs4357923, rs12589674, rs2174147, rs8009420, rs17815373, rs11161719, rs10515601, rs1874848, rs78323632, rs111851441, rs9920618, rs11740072, rs78252085 rs4845054, rs1086013, rs4508236, rs9458512, rs17147461, rs78341108, rs6866169, rs72681708, rs4912453, rs12120406, or rs8056050.

5. The method of claim 1, wherein the personalized health care of the individual patient relates to a baseline diagnosis of Alzheimer's disease with respect to the individual patient such that the integrated report is a baseline integrated report for the individual patient.

6. The method of claim 1, wherein the personalized health care of the individual patient relates to a longitudinal monitoring of Alzheimer's disease within the individual patient such that the integrated report is an integrated longitudinal safety/efficacy monitoring report.

7. The method of claim 4, wherein the personalized health care of the individual patient relates to biomarkers of the individual patient, and analyzing the one or more data streams includes predictive analytics such that the integrated report is a predictive analytics report.

8. The method of claim 7, wherein the predictive analytics is based on a neural network machine learning algorithm.

9. The method of claim 7, wherein the predictive analytics predicts Alzheimer's disease at a pre-symptomatic stage.

10. The method of claim 7, wherein the predictive analytics predicts a response of the individual patient to a particular therapy.

11. The method of claim 1, further comprising applying the personalized therapy to the individual patient, wherein the personalized therapy is an antibody against the BMP-4 protein or functional fragment thereof when the individual patient does not test positive or is determined to be a non-carrier for the rs4891826 (G) SNP.

12. The method of claim 7, wherein the predictive analytics is based on a social network analysis (SNA) of the gene/protein molecular network with respect to the one or more selected SNPs and wherein the personalized therapy is small molecule oncology kinase inhibitor selected based on the SNA.

13. The method of claim 1, further comprising applying the personalized therapy to the individual patient, wherein the personalized therapy is a small molecule oncology kinase inhibitor when the individual patient does not test positive or is determined to be a non-carrier for the rs4891826 (G) SNP.

14. The method of claim 1, further comprising applying the personalized therapy to the individual patient, wherein the personalized therapy is an antibody against the ALCAM/CD166 protein or functional fragment thereof when the individual patient does not test positive or is determined to be a non-carrier for the rs2030515 (G) SNP.

15. The method of claim 1, further comprising applying the personalized therapy to the individual patient, wherein the personalized therapy is an mTOR inhibitor when the individual patient does not test positive or is determined to be a non-carrier for the rs2030515 (G) SNP.

16. The method of claim 1, further comprising applying the personalized therapy to the individual patient, wherein the personalized therapy is a combination therapy of an anti-BMP-4 antibody or functional fragment thereof and an mTOR inhibitor when the individual patient does not test positive or is determined to be a non-carrier for both the rs4891826 (G) and rs2030515 (G) SNPs.

17. The method of claim 1, further comprising applying the personalized therapy to the individual patient, wherein the personalized therapy is CRISPR mediated gene editing or trans-epigenetic modulation in the RTTN, ALCAM, DMXL2, DYNLL1 genes based on the testing for said rs4891826 (G), rs2030515 (G), rs7164265 (C), or rs993900 (A) SNPs.

18. The method of claim 1, further comprising applying the personalized therapy to the individual patient, wherein the personalized therapy is CRISPR mediated gene editing in the ALCAM gene when the individual patient does not test homozygous for the rs2030515 (G) SNP, and wherein the gene editing may be applied to neural stem cells of the individual patient, such that the gene edited stem cells carry two copies of the rs2030515 allele so as to be homozygous, and wherein the gene edited stem cells are then further delivered into the individual patient's brain using image-guided delivery into targeted brain structures.

19. The method of claim 1, further comprising applying the personalized therapy to the individual patient, wherein the personalized therapy is an antisense oligonucleotide (ASO) or short-interfering RNA (siRNA) therapy targeting the ALCAM/CD166 gene, when the individual patient does not test positive or is determined to be a non-carrier for the rs2030515 (G) SNP.

20. The method of claim 1, further comprising:
detecting the at least one SNPs in a human subject from assaying a combination of SNPs by:
a) obtaining a nucleic acid sample from said human subject;
b) genotyping the sample for a combination of Alzheimer's disease associated genes(s) RTTN, ALCAM/CD166, DMXL2, and DYNLL1, said combination of SNP alleles being the following: rs4891826 (G), rs2030515 (G), rs7164265 (C), and rs993900 (A); and
c) detecting in said nucleic acid sample the presence of at least one of: a G for rs4891826, a G for rs2030515, a C for rs7164265, or an A for rs993900.

21. A method of delivering information-enabled personalized health care with respect to early Alzheimer's disease in a clinical, non-research setting, the method comprising:
provisioning, using one or more servers, a healthcare social network particular to providing personalized health care for an individual patient, the healthcare social network configured to:
accept the individual patient as a new patient in the healthcare social network,
add content data for the individual patient, the content data including one or more physical measurements from diagnostic testing performed on the individual patient using testing equipment of a testing system coupled with the healthcare social network,
specify recipients within the healthcare social network particular to the individual patient for delivery of the content data, and
provide a secure interface for multiple participants particular to the individual patient to exchange bidirectional secure correspondence within the healthcare social network regarding the personalized health care of the individual patient and transfer the content data there between based on permissions within the healthcare social network,
inputting, using one or more processors, one or more data streams to the healthcare social network, each of the data streams related to health care of the individual patient, wherein one or more of the data streams include the content data that includes results from the diagnostic testing of the individual patient, wherein at least one of the data streams includes the content data from genetic testing for at least one single-nucleotide polymorphism (SNP), and further includes content data of one or more of a voxel-based imaging quantitation, a cerebrospinal fluid (CSF) assay for tau protein or amyloid beta peptide of the individual patient derived from a spinal tap procedure, or a blood test for Alzheimer's disease, performed on the individual patient;
generating, using one or more processors, a diagnostic profile for the individual patient, the diagnostic profile being based on the content data of the detected at least one SNP;
curating, using the one or more processors, the diagnostic profile by presenting the diagnostic profile with contextual medical information to obtain a curated diagnostic profile;
generating, using the one or more processors, an integrated report for presentation to a physician of the individual patient using the curated diagnostic profile, the integrated report for providing a personalized therapy for the individual patient with respect to the curated diagnostic profile; and
applying the personalized therapy to the individual patient, wherein the personalized therapy includes at least one of:
a) an antibody against the BMP-4 protein or functional fragment thereof when the individual patient does not test positive or is determined to be a non-carrier for the rs4891826 (G) SNP;
b) a small molecule oncology kinase inhibitor selected based on predictive analytics by a social network analysis (SNA) of the gene/protein molecular network with respect to the one or more detected SNPs;
c) a small molecule oncology kinase inhibitor when the individual patient does not test positive or is determined to be a non-carrier for the rs4891826 (G) SNP;
d) an antibody against the ALCAM/CD166 protein or functional fragment thereof when the individual patient does not test positive or is determined to be a non-carrier for the rs2030515 (G) SNP;
e) an mTOR inhibitor when the individual patient does not test positive or is determined to be a non-carrier for the rs2030515 (G) SNP;

f) a combination therapy of an anti-BMP-4 antibody or functional fragment thereof and an mTOR inhibitor when the individual patient does not test positive or is determined to be a non-carrier for both the rs4891826 (G) and rs2030515 (G) SNPs;
g) CRISPR mediated gene editing or trans-epigenetic modulation in the RTTN, ALCAM, DMXL2, DYNLL1 genes based on the testing for said rs4891826 (G), rs2030515 (G), rs7164265 (C), or rs993900 (A) SNPs;
h) CRISPR mediated gene editing in the ALCAM gene when the individual patient does not test homozygous for the rs2030515 (G) SNP, and wherein the gene editing may be applied to neural stem cells of the individual patient, such that the gene edited stem cells carry two copies of the rs2030515 allele so as to be homozygous, and wherein the gene edited stem cells are then further delivered into the individual patient's brain using image-guided delivery into targeted brain structures; or
i) an antisense oligonucleotide (ASO) or short-interfering RNA (siRNA) therapy targeting the ALCAM/CD166 gene, when the individual patient does not test positive or is determined to be a non-carrier for the rs2030515 (G) SNP.

* * * * *